(12) United States Patent
Yamamoto

(10) Patent No.: US 6,299,630 B1
(45) Date of Patent: Oct. 9, 2001

(54) ENDOSCOPIC PROCEDURAL DEVICE

(75) Inventor: Tetsuya Yamamoto, Hidaka (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/411,082

(22) Filed: Oct. 4, 1999

(30) Foreign Application Priority Data

Oct. 8, 1998 (JP) .................................. 10-286454
Sep. 24, 1999 (JP) .................................. 11-270918

(51) Int. Cl.⁷ .................................................. A61B 17/28
(52) U.S. Cl. .......................... 606/205; 606/208; 606/170
(58) Field of Search .................... 606/170, 205, 606/207, 206, 208, 167

(56) References Cited

U.S. PATENT DOCUMENTS 5,133,727 * 7/1992 Bales et al. ........................... 606/170
5,666,965   9/1997 Bales et al. .
5,810,876 * 9/1998 Kelleher ................................ 606/205

FOREIGN PATENT DOCUMENTS 10-118089A  5/1998 (JP) .
10-179601   7/1998 (JP) .

* cited by examiner

*Primary Examiner*—Henry J. Recla
*Assistant Examiner*—Julian W. Woo
(74) *Attorney, Agent, or Firm*—Frishauf, Holtz, Goodman, Langer & Chick, P.C.

(57) ABSTRACT

An endoscopic procedural device of the present invention comprises an insert section that has an inside hole extending along its axial direction, and which has flexibility to enable its insertion through a forceps-channel of an endoscope, at least one operating wire that is inserted in the inside hole of the insert section, and which is freely moved forward or backward along the axial direction of the insert section, an operating section which is used for moving an operating wire forward or backward, at least one procedural member that is mounted to a distal end of the procedural section holding member in a rotatable manner, and which has one through-hole at its proximal end side to which one of the operating wires is connected, wherein the one through-hole has a first opening end on one side of a procedural member at a position farther from the center axis of the insert section, and a second opening end on the other side of the procedural member at a position closer to the center axis of the insert section, and a distal end portion of an operating wire is not only inserted into the one through-hole toward the center axis side of the insert section from the first opening end, but protruded outside the one through-hole from the second opening end and the protruded distal end portion of the operating wire is positioned in the vicinity of the second opening end.

20 Claims, 24 Drawing Sheets

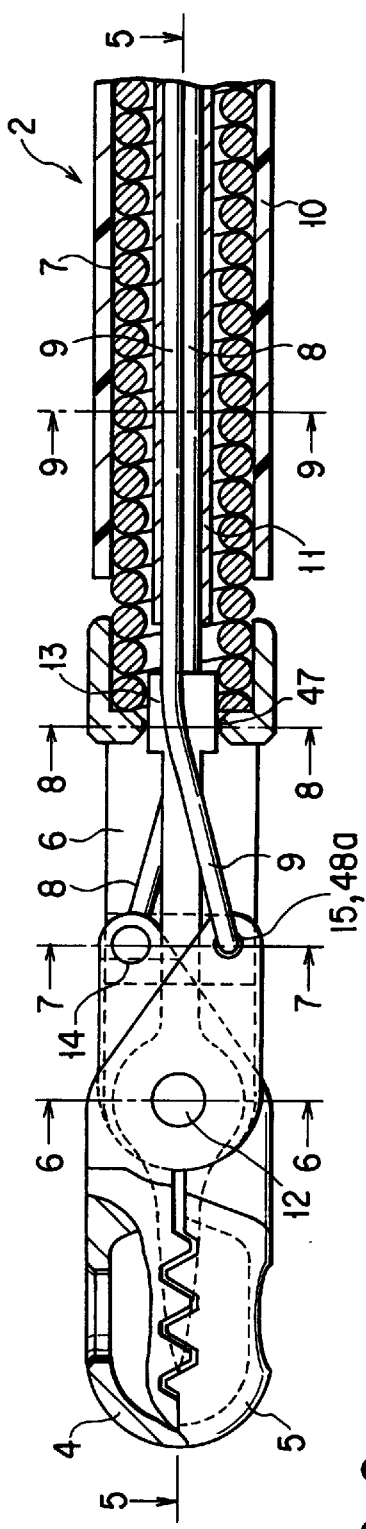
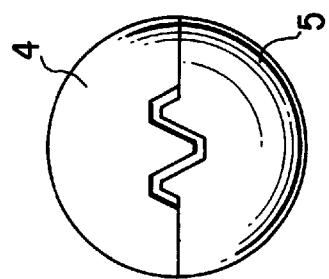
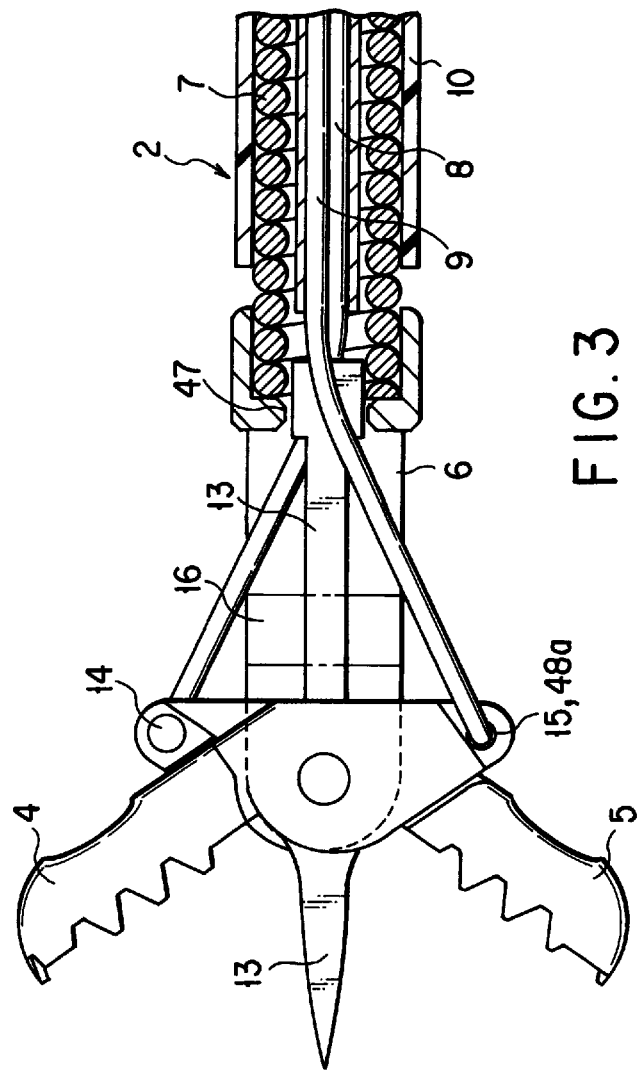
FIG. 2
FIG. 4
FIG. 3

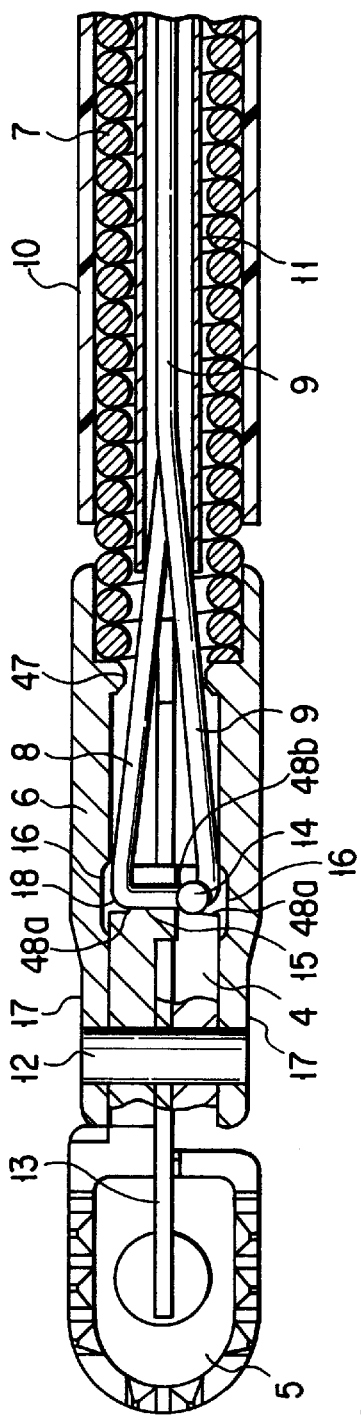
FIG. 5
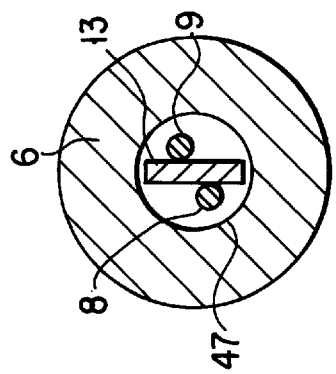
FIG. 8
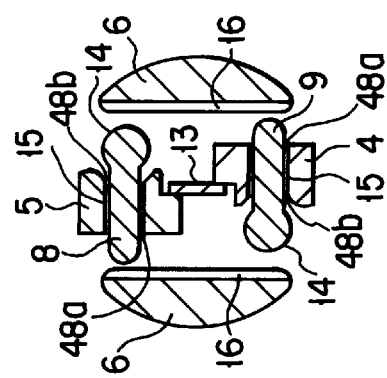
FIG. 7
FIG. 6

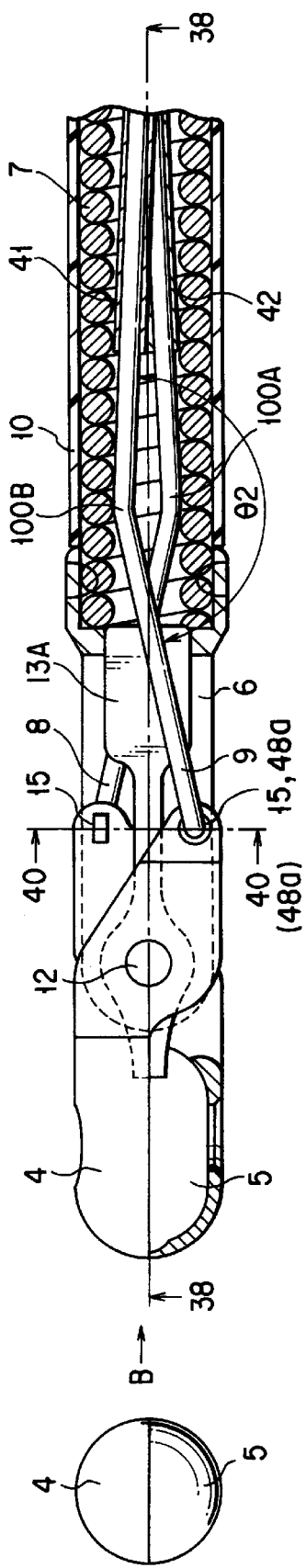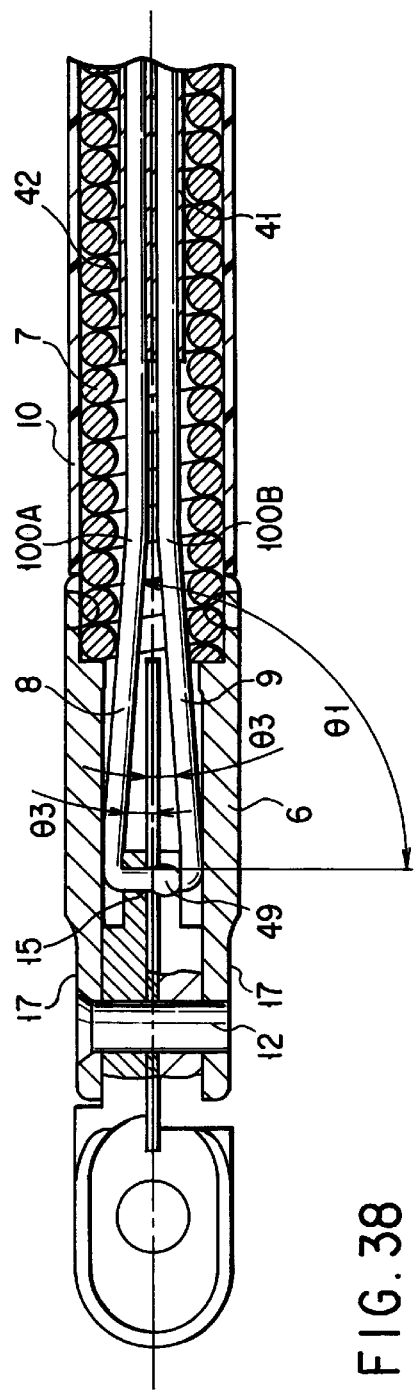
FIG. 37
FIG. 38
FIG. 39

ENDOSCOPIC PROCEDURAL DEVICE

BACKGROUND OF THE INVENTION

The present invention relates to an endoscopic procedural device for performing surgical procedures with tissue or the like of a body while being inserted into a body cavity through a forceps-channel of an endoscope.

For example, an endoscopic procedural device is provided with a flexible insert section that can be inserted through a forceps-channel of an endoscope. An operating wire is inserted in the interior of the insert section along its axial direction in such a way that the wire can freely moved forward or backward. The operating wire is connected not only to an operating section at a proximal end of the insert section, but to a procedural member at a distal end of the insert section. With such a construction, the operating wire is moved forward or backward and the procedural member is opened or closed in response to operations of the operating section.

Endoscopic procedural devices of this kind have been disclosed, for example, in U.S. Pat. Nos. 5,666,965 and 5,133,727, and Jpn. Pat. Appln. KOKAI Publication Nos. 10-118089 and 10-179601.

In U.S. Pat. Nos. 5,666,965 and 5,133,727, and Jpn. Pat. Appln. KOKAI Publication No. 10-118089A, a connecting structure, in which a procedural member and an operating wire inserted though an insert section so that the wire can freely moved forward or backward, are connected, the operating wire is passed through a hole formed in a procedural member and a distal end of the operating wire that has passed through the hole is sharply bent and fixed on the procedural member. In Jpn. Pat. Appln. KOKAI Publication No. 10-179601, link wires are respectively passed through a pair of connecting holes formed at the proximal end sides of respective procedural members and both ends of each link wire are fixed on a distal end of an operating wire.

However, in the connecting structure of the former documents, as shown in FIG. 33, in a case where an endoscopic procedural device a is inserted through an inside hole of a forceps-channel c of the endoscope b and a procedural member d is protruded into a body cavity, an inner surface of the forceps-channel channel c is heavily damaged and in the worst case, a hole is opened through the wall portion of the forceps-channel to destroy the endoscope b by an edge f of the distal end of the operating wire e for opening or closing of the procedural member d if the endoscope b is bent and thereby, the forceps-channel c is curved like an arc with a large radius of curvature. In this case, such troubles may lead to significant repair costs.

Further, in the connecting structure of the latter document, since two pieces of link wires are virtually connected to one procedural member and two procedural members are activated with the four pieces of link wires in total, movements of the endoscopic procedural device becomes heavy due to excessively high rigidity of the link wires and the operability feeling is problematically deteriorated.

BRIEF SUMMARY OF THE INVENTION

It is an object of the present invention to provide an endoscopic procedural device that has no chance to damage a forceps-channel of an endoscope even when the endoscope is bent, which has not only a good operability feeling, but a simple construction easy to assemble and to produce at a low cost, and which secures safety in use.

The object of the present invention is achieved by the following endoscopic procedural device. That is, an endoscopic procedural device according to the present invention comprises: an insert section that has an inside hole extending along its axial direction, and which has flexibility to enable its insertion through a forceps-channel of an endoscope; at least one operating wire that is inserted in the inside hole of the insert section, and which is freely moved forward or backward along the axial direction of the insert section; an operating section that is connected to a proximal end of the insert section, and which is used for moving the operating wire forward or backward; a procedural section holding member connected to a distal end of the insert section; at least one procedural member that is mounted to a distal end of the procedural section holding member in a rotatable manner, and which has one through-hole at its proximal end side, to which one of the operating wires is connected, wherein the one through-hole has a first opening end, on one side of a procedural member, at a position farther from the center axis of the insert section, and a second opening end, on the other side of the procedural member, at a position closer to the center axis of the insert section; and a distal end portion of an operating wire is not only inserted into the one through-hole toward the center axis side of the insert section from the first opening end, but protruded outside the one through-hole from the second opening end and the protruded distal end portion of the operating wire is positioned in the vicinity of the second opening end.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a sectional view of a distal end side of an insert section of the endoscopic procedural device of FIG. 1 in a state in which a biopsy cup is closed;

FIG. 3 is a sectional view of a distal end side of an insert section of the endoscopic procedural device of FIG. 1 in a state in which a biopsy cup is opened;

FIG. 4 is a front view of a biopsy cup;

FIG. 5 is a sectional view taken along the line 5—5 of FIG. 2;

FIG. 6 is a sectional view taken along the line 6—6 of FIG. 2;

FIG. 7 is a sectional view taken along the line 7—7 of FIG. 2;

FIG. 8 is a sectional view taken along the line 8—8 of FIG. 2;

FIG. 37 is a sectional view of a distal end side of an insert section of the endoscopic procedural device of FIG. 36 in a state in which a biopsy cup is closed;

FIG. 38 is a sectional view taken along the line 38—38 of FIG. 37;

FIG. 39 is a view in a direction of arrow B of FIG. 37;

DETAILED DESCRIPTION OF THE INVENTION

Below, description will be made of embodiments of the present invention with reference to the accompanying drawing.

Figure 1:
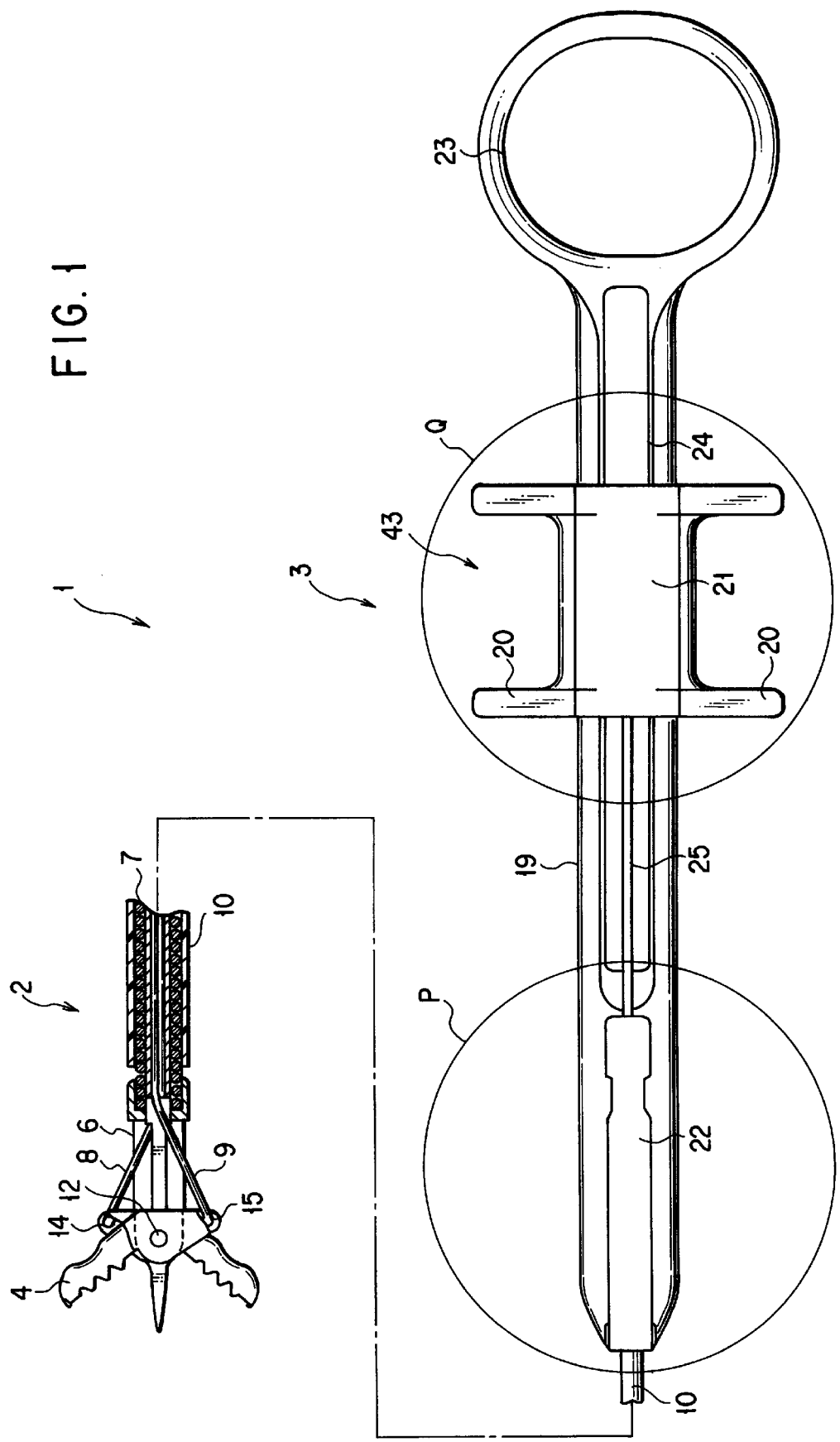
FIG. 1 is an overall view of construction of an endoscopic procedural device (bioptome) according to a first embodiment of the present invention.

FIGS. 1 to 25 show the first embodiment of the present invention. As shown in FIG. 1, a bioptome 1 as an endoscopic procedural device according to this embodiment comprises: an insert section 2 that has a flexibility enough to be inserted through a forceps-channel of an endoscope; and an operating section 3 connected to a proximal end of the insert section 2. As shown in FIGS. 2 and 3, the insert section 2 comprises: a coil 7 having an inside hole; an outside tube 10 covering an outer surface of the coil 7; an inside tube 11 provided in the inside hole of the coil 7 and freely movable forward or backward; and two operating wires 8 and 9 inserted and freely movable forward or backward in the inside hole of the inside tube 11.

The outside tube 10 is produced by applying a thermal shrinkage tube or performing tubing molding on an outer surface of the coil 7. As materials of the outside tube 10, there can be used, for example, high density polyethylene, a mixture of high density polyethylene and low density polyethylene, a mixture of low density polyethylene and polypropylene, and others, which are available at a low cost and excellent in insertion ability through the forceps-channel of the endoscope.

Figure 34:
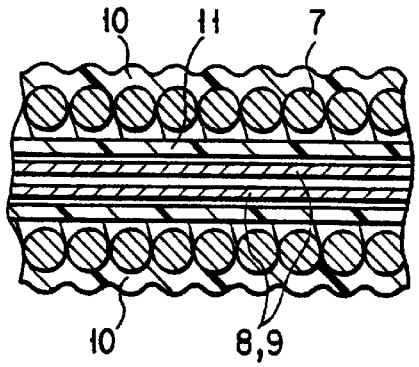
FIG. 34 is a sectional view showing a second modification example of the insert section of the endoscopic procedural device of FIG. 1.
Figure 35:
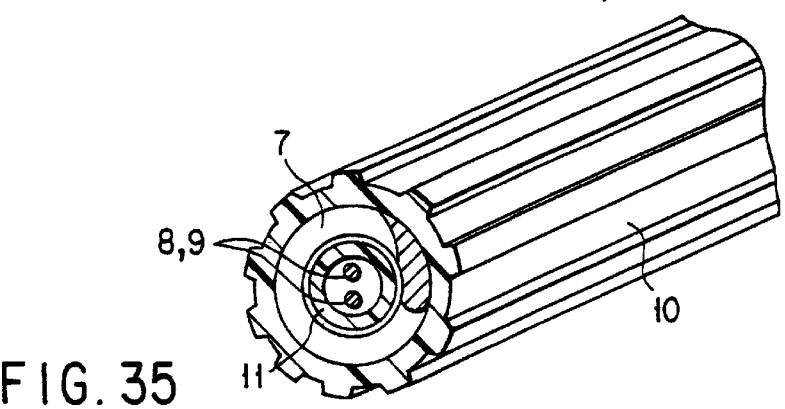
FIG. 35 is a sectional view showing a third modification example of the insert section of the endoscopic procedural device of FIG. 1.

An outer surface of the outside tube 10, as shown in FIG. 34, may have surface irregularity as is produced by transfer of an outer surface topography of the coil 7 to the outer surface. Besides, a plurality of parallel ridges may be arranged ex tending along longitudinal directions on an outer surface of the outside tube 10, as shown in FIG. 35. Either the outside tube 10 or the inside tube 11 need not necessarily be provided. Further, instead of providing the inside tube 11, a resin similar to material of the inside tube 11 may be applied on an inner surface of the coil 7 to form a coat.

Figure 10:
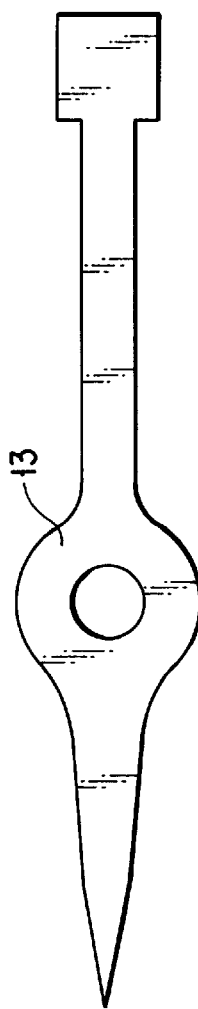
FIG. 10 is a side view of a needle of the endoscopic procedural device of FIG. 1.

A cup holding member 6 is provided as a procedural section holding member at the distal end of the coil 7. The cup holding member 6 is fixed to the coil 7 in an engaging manner by means of laser welding, soldering, caulking or the like. A pair of biopsy cups 4 and 5 serving as a procedural member, as shown in FIG. 6, are mounted in the vicinity of the distal end of the cup holding member 6 so as to be freely rotatable about a pin 12. As shown in FIGS. 2, 3, 5 and 6, a needle 13 is disposed so as to be sandwiched between the biopsy cups 4 and 5. The needle 13 has a shape, as shown in FIG. 10, and the distal end side of the needle 13 is mounted to the pin 12. The proximal end side of the needle 13, as shown in FIG. 8, is engaged in a hole 47 formed in the vicinity of the proximal end of the cup holding member 6. In order to increase a needling performance of a needle 13, a thickness of a plate portion of the needle 13 is roughly set in the range of 0.05 mm to 0.3 mm. The needle 13 is produced by press, photo-etching, forging or the like.

Figure 9:
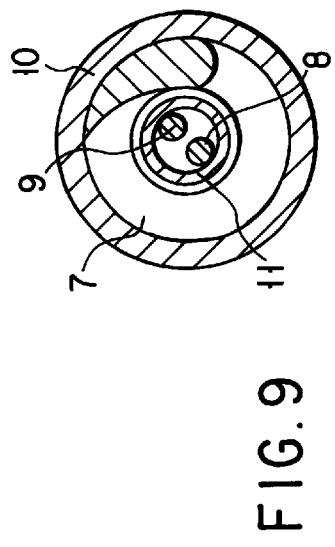
FIG. 9 is a sectional view taken along the line 9—9 of FIG. 2.
Figure 25:
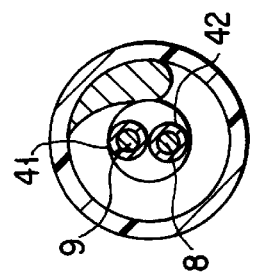
FIG. 25 is a sectional view taken along the line 25—25 of FIG. 24.
Figure 24:
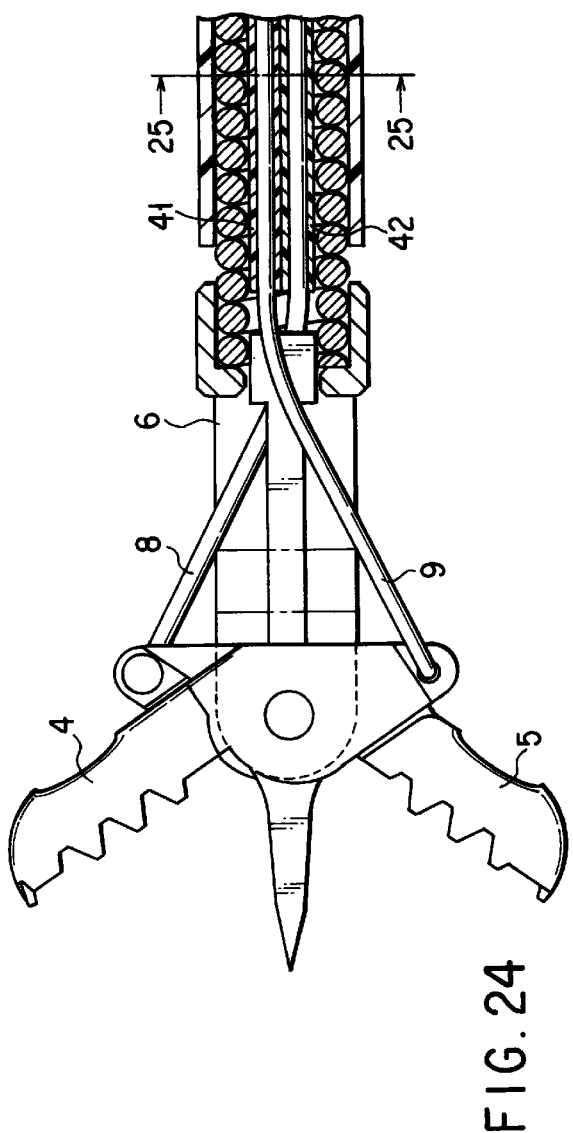
FIG. 24 is a sectional view showing a first modification example of an insert section of the endoscopic procedural device of FIG. 1.
Figure 26A:
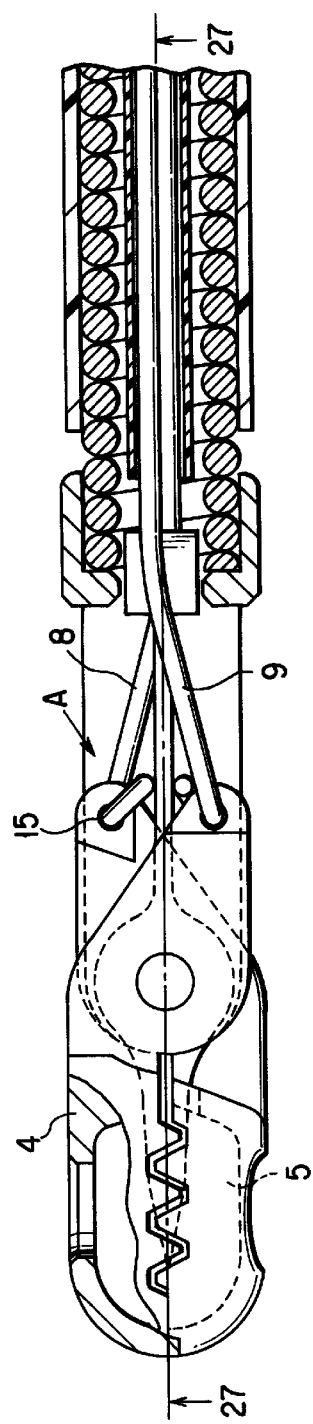
FIG. 26A is a sectional view of an insert section of an endoscopic procedural device according to a second embodiment of the present invention.
Figure 26B:
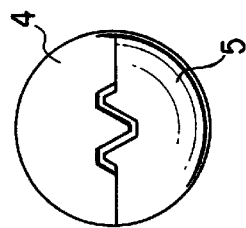
FIG. 26B is a front view of the insert section of FIG. 26A.
Figure 27:
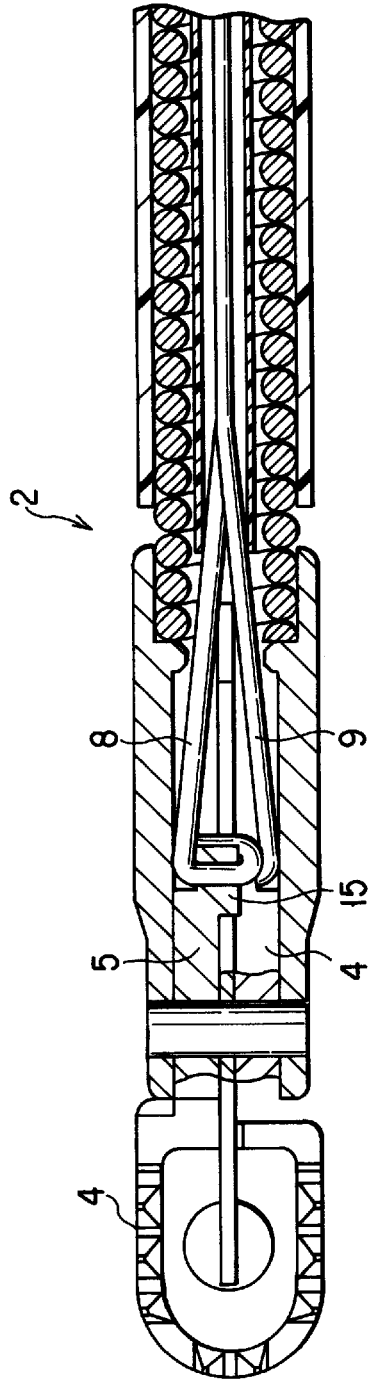
FIG. 27 is a sectional view taken along the line 27—27 of FIG. 26A.
Figure 30:
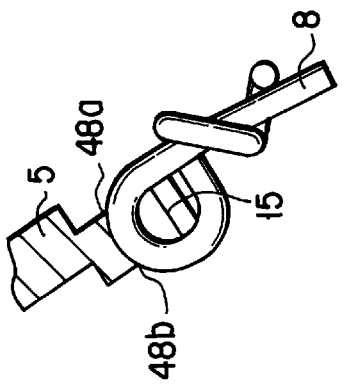
FIG. 30 is a view of a second modification example of the connecting state shown in FIG. 28.
Figure 29:
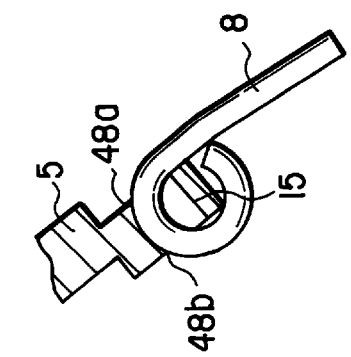
FIG. 29 is a view of a first modification example of the connecting state shown in FIG. 28.

The inside tube 11 is coated in an outer surface of the operating wires 8 and 9 that are positioned in the coil 7. The operating wires 8 and 9 are only inserted in the inside hole of the inside tube 11 as shown in FIG. 9 but not fixed to the inside tube 11. As shown in FIGS. 24 and 25, the operating wires 8 and 9 may be coated with respective inside tubes 41 and 42. In this case, the inside tubes 41, 42 are preferably formed with thermal shrinkage tubes or by application of tubing molding on the outer surfaces of the operating wires 8 and 9. Both opening ends of the inside tubes 41 and 42 may be hermetically sealed using a resin, an adhesive or the like as needs come up.

As shown in FIGS. 5 and 7, the distal end portions of the operating wires 8 and 9 are bent at an almost right angle and the distal end portions are respectively inserted into holes (through-holes) 15 formed in the proximal end sides of the biopsy cups 4 and 5. In this case, the distal end portions of the bent operating wires 8 and 9 are respectively inserted into the holes 15 from first opening ends 48a of the holes 15 deviated from the center axis of the insert section 2 toward the center axis side of the insert section 2 and the distal end portions thus inserted are respectively protruded outside the holes 15 from second opening ends 48b of the hole 15. In other words, the holes 15 respectively have the first opening ends 48a on one side of the biopsy cups 4 and 5 at a position farther from the center axis of the insert section 2, and respectively have the second opening ends 48b on the other side of the biopsy cups 4 and 5 at a position closer to the center axis of the insert section 2, wherein the distal end portions of the operating wires 8 and 9 are respectively first inserted into the holes 15 through the first opening ends 48a of the holes 15 toward the center axis side of the insert sections 2 and then the distal ends are respectively protruded outside the holes 15 from the second opening ends 48b of the holes 15 and the distal end portions of the operating wires 8 and 9 are respectively positioned in the vicinity of the second opening ends 48b.

In order to prevent the operating wires 8 and 9 from being slipped off from the holes 15, the distal ends of the operating wires 8 and 9 protruded outside the holes 15 respectively have stoppers 14 in an almost spherical shapes formed by means of plasma welding, laser welding or the like. The stoppers 14 are respectively formed by transforming the distal ends of the operating wire 8 and 9 into spherical shapes by welding, or by fixing pieces already formed in spherical shapes at the distal ends thereof by means of application of an adhesive, welding, caulking or the like.

Both end faces of a pin 12 are fixedly attached to a cup holding member 6 by means of laser welding or caulking as shown in FIGS. 5 and 6. As shown in FIG. 5, the diameter of a distal end portion 17 of the cup holding member 6 to which the pin 12 is fixed is set to be smaller compared with the other parts and a diameter is changed stepwise. With such a structure, if burr occurs after welding or caulking, a forceps-channel of the endoscope is never damaged.

In order to increase clearance between the stoppers 14 and the cup holding member 6, recesses 16 are formed on surfaces of the middle area of the cup holding member 6 as shown in FIGS. 5 and 7. Of course, if no need for large clearance arises, the recesses 16 is not required to be provided.

The outside tube 10 and the inside tube 11 (41 and 42) are made of resin materials or a mixture selected from, polytetrafluoroethylene (PTFE), tetrafluoroethylene-perfluoroalkoxy ethylene resin (PFA), tetrafluoroethylene-hexafluoropropylene resin (FEP), polyethylene, polypropylene, polyethylene-terephthalate, ethylene-vinyl acetate copolymer, polyolefin, polyamide, vinyl chloride, latex, natural rubber and others.

Biopsy cups 4 and 5, and the cup holding member 6 are made of a metal material or a resin material. In the case of metals, the members 4, 5 and 6 are made of each of the following metals or alloys thereof: stainless, aluminum, nickel, brass, titanium, iron, phosphor bronze, tungsten, gold, silver, copper, SF20T (ferritic stainless steel: chemical composition $C \leq 0.05$ wt %, $Si \leq 1$ wt %, $Mn \leq 2$ wt %, $P \leq 0.05$ wt %, $S \geq 0.15$ wt %, $Cr=19$ to 21 wt %, $Mo=1.5$ to 2.5 wt %, $Pb=0.1$ to 0.3 wt %, $Te=0.01$ to 0.07 wt %) and others. In the case of a resin material, the members 4, 5 and 6 are made of polysulfone, polyphenylsulfone, polyether imide, polytetrafluoroethylene (PTFE), tetrafluoroethylene-perfluoroalkoxy ethylene resin (PFA), tetrafluoroethylene-hexafluoropropylene resin (FEP), polyacetal, poly(ether ether ketone), polyolefin, polycarbonate, acrylonitrile butadiene-styrene resin, polyamide, vinyl chloride, latex, liquid crystal polymer and others.

Further, the coil 7, the operating wires 8 and 9, and the needle 13 are made of each of the following metals and alloys thereof: stainless, aluminum, nickel, brass, titanium, iron, phosphor bronze, tungsten, gold, silver, copper and others.

Figure 11:
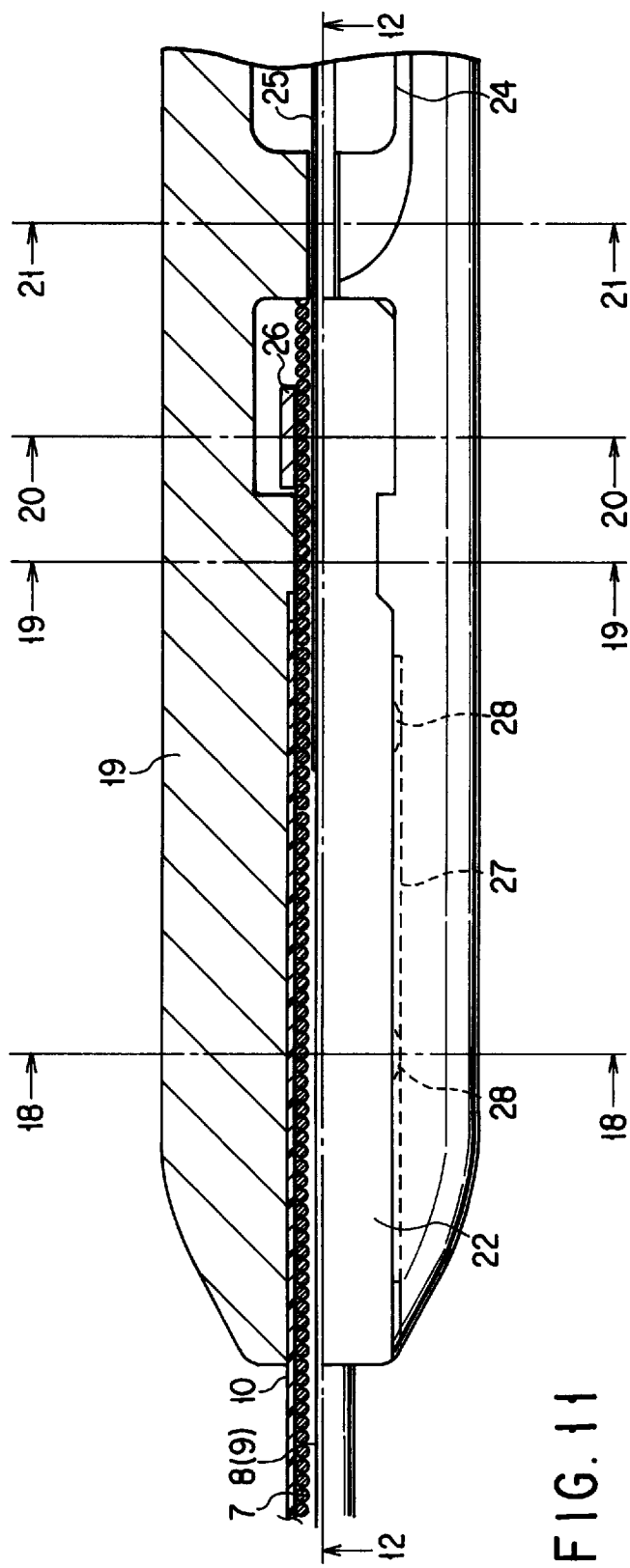
FIG. 11 is an enlarged sectional view of part P of FIG. 1 (the upper half only is shown in section)
Figure 12:
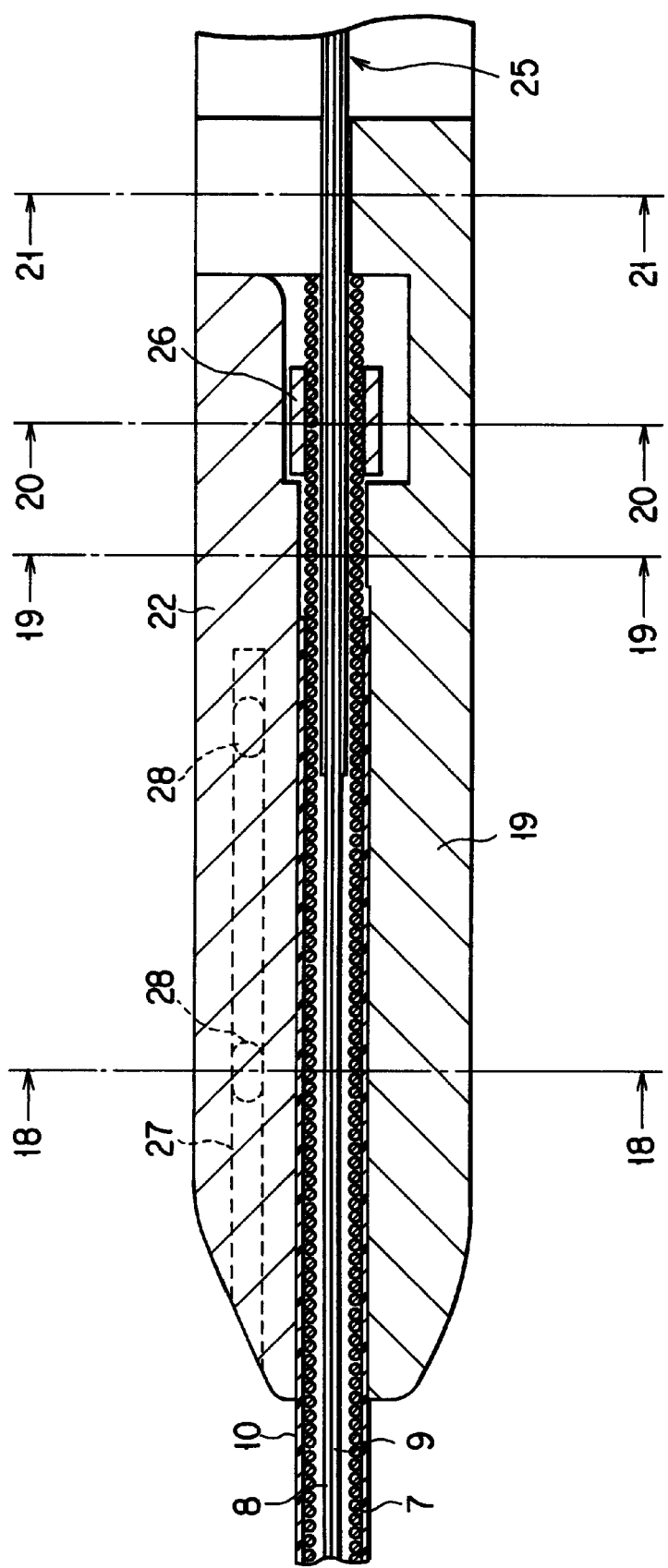
FIG. 12 is a sectional view taken along the line 12—12 of FIG. 11.
Figure 20:
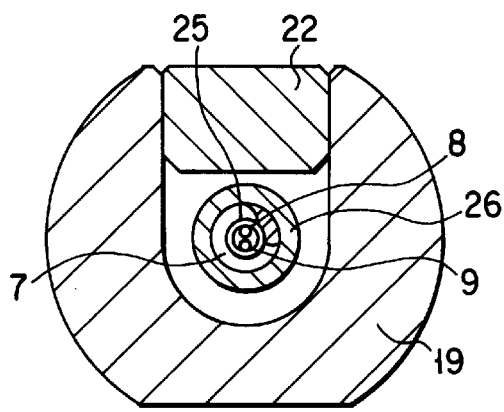
FIG. 20 is a sectional view taken along the line 20—20 of FIGS. 11 and 12.
Figure 21:
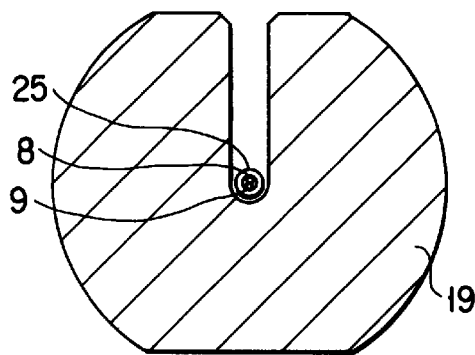
FIG. 21 is a sectional view taken along the line 21—21 of FIGS. 11 and 12.

The operating section 3, as shown in FIG. 1, comprises: an operating section body 19 and a slider 43. A stopper 26 having a cylindrical shape is fixed to the proximal end side of the coil 7 as shown in FIGS. 11, 12 and 20. In this case, the stopper 26 is fixed to the coil 7 by means of autosplicing, caulking, welding or the like. A body cover 22 is fixed to the operating section body 19 as shown in FIGS. 11, 12 and 18 to 20. In this case, small protrusions 28 formed on the body cover 22 are engaged with grooves 27 formed on the operating body 19 and thereby, the body cover 22 is fixed to the operating section body 19. The proximal end side of the insert section 2 including the stopper 26 goes into the operating section body 19, the body cover 22 is fixed to the operating section body 19 and thus, the insert section 2 is fixed to the operating section 3.

Figure 13:
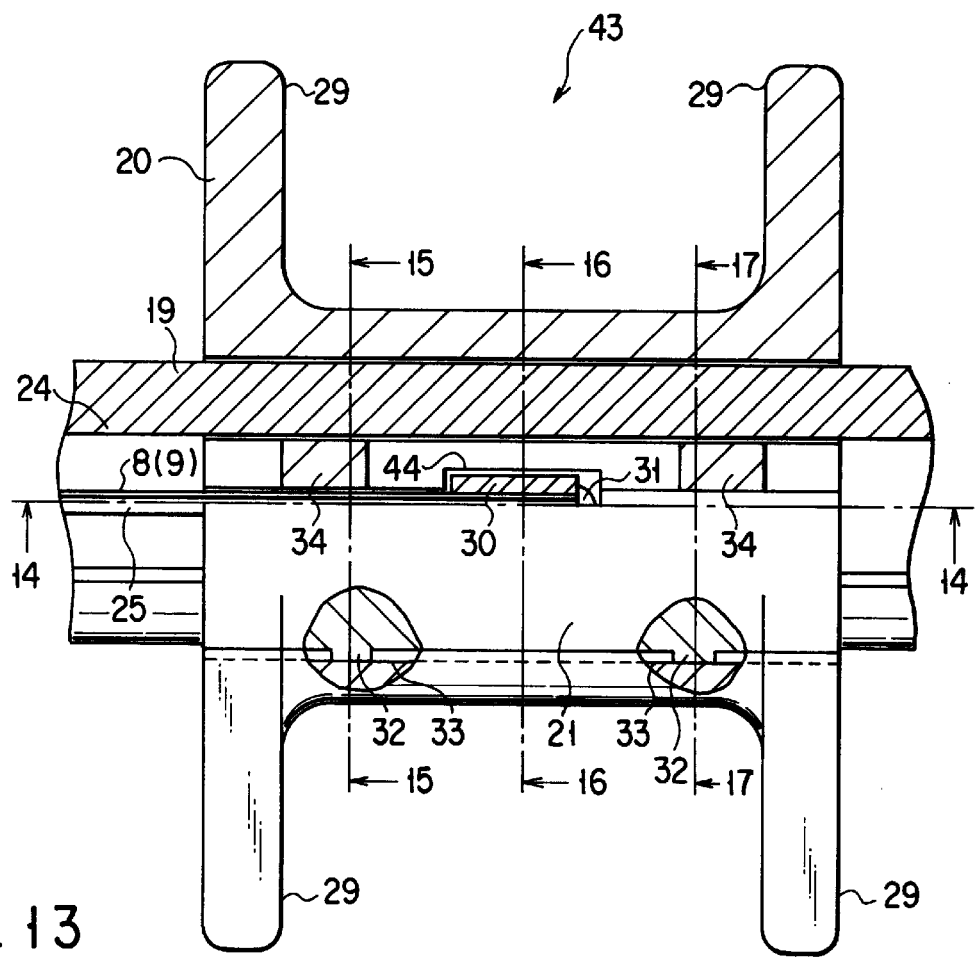
FIG. 13 is an enlarged sectional view of part Q of FIG. 1 (the upper half only is shown in section)
Figure 14:
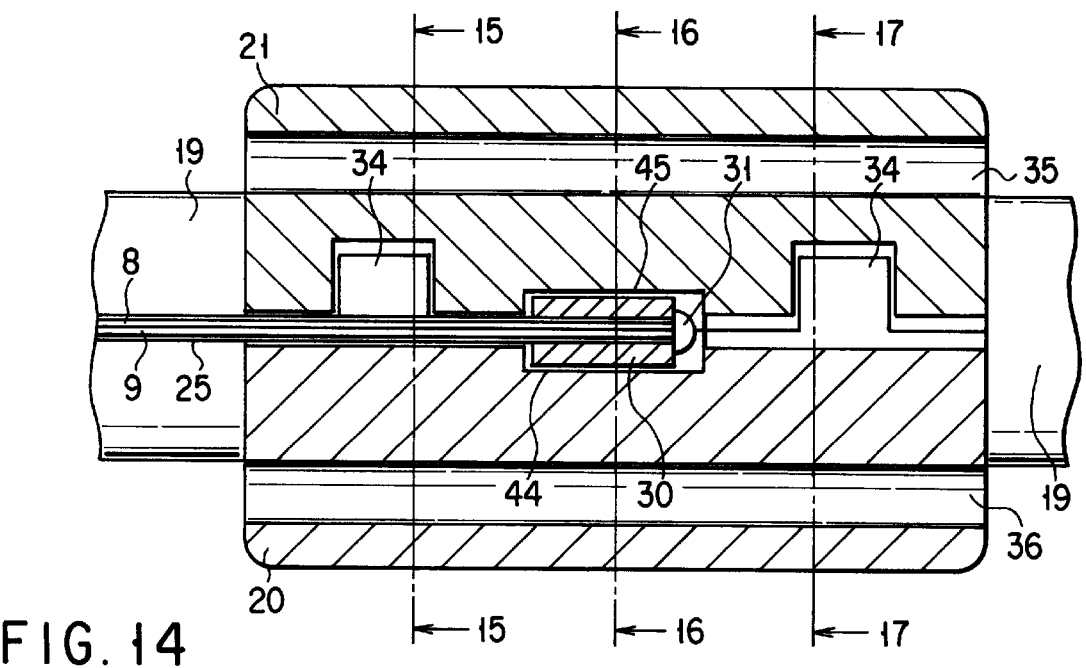
FIG. 14 is a sectional view taken along the line 14—14 of FIG. 13.

The proximal end sides of the operating wires 8 and 9 are inserted through the inside hole of an operating pipe 25 as shown in FIGS. 11, 12, 15 and 16. Further, as shown in FIGS. 13 and 14, the proximal end portion of the operating pipe 25 is fittingly inserted into the inside hole of a stopper 30 having a cylindrical shape. The operating wires 8 and 9, the operating pipe 25 and the stopper 30 are integrated into one body through mutual joining by means of plasma welding, laser welding or the like at the proximal end face portion 31 of the stopper 30.

As shown in FIGS. 13 and 14 to 17, a slider 43 comprises: a slider body 20; and a slider cover 21, and can slide on rails having a half-moon like shape of the operating section body 19 having a groove 24. A finger catch 20 is formed on the slider body 20. Grooves 33 formed on the slider body 20 and small protrusions 32 formed on the slider cover 21 are engaged with each other, and the stopper 30 is engaged in recesses 44 and 45 respectively formed in an almost center portions of the slider body 20 and the slider cover 21, whereby the proximal ends of the operating wires 8 and 9 including the operating pipe 25 and the stopper 30 are fixed to the slider 43.

Figure 15:
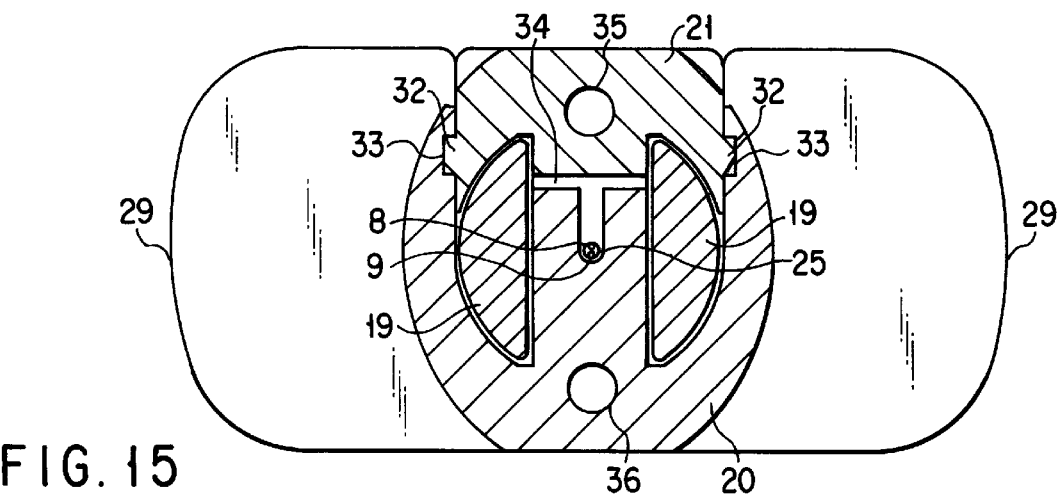
FIG. 15 is a sectional view taken along the line 15—15 of FIG. 13.
Figure 16:
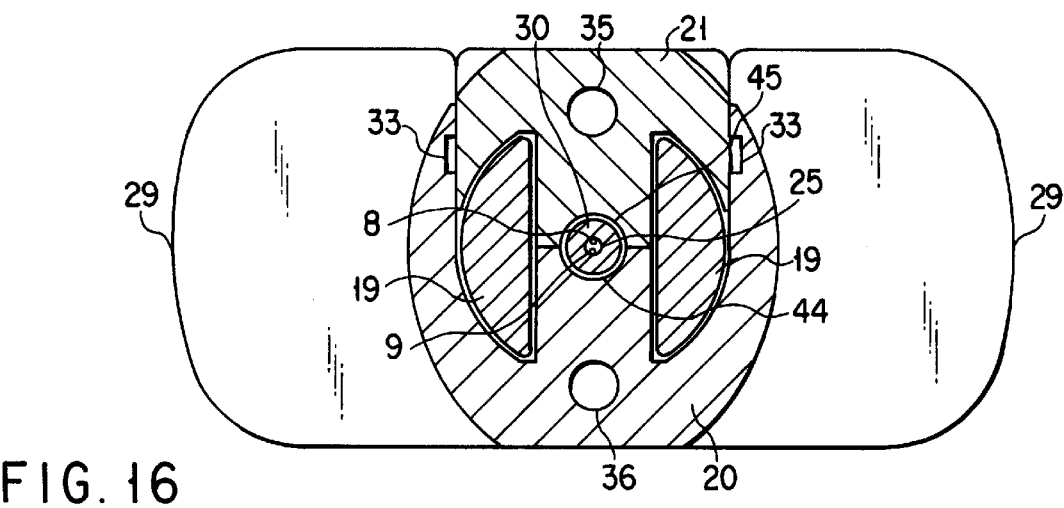
FIG. 16 is a sectional view taken along the line 16—16 of FIG. 13.
Figure 17:
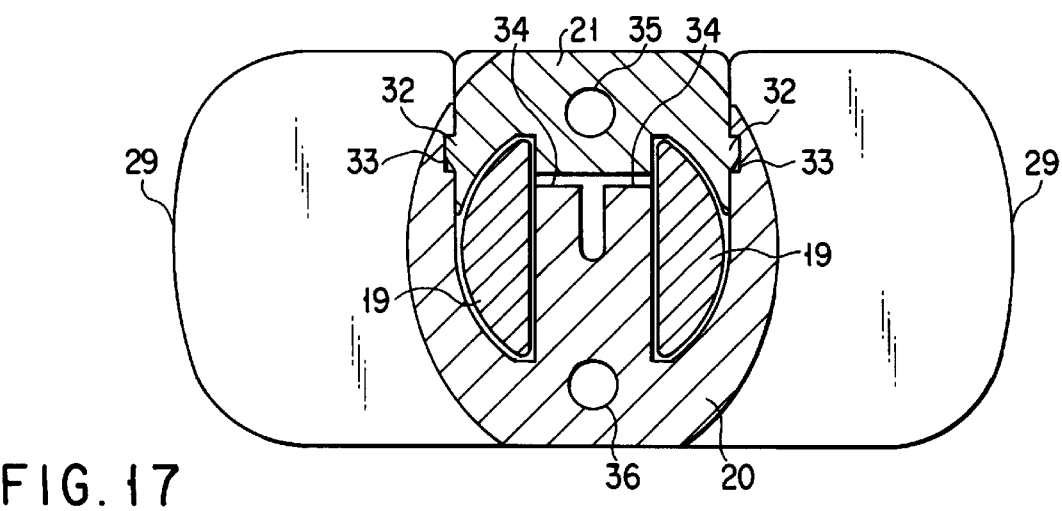
FIG. 17 is a sectional view taken along the line 17—17 of FIG. 13.
Figure 18:
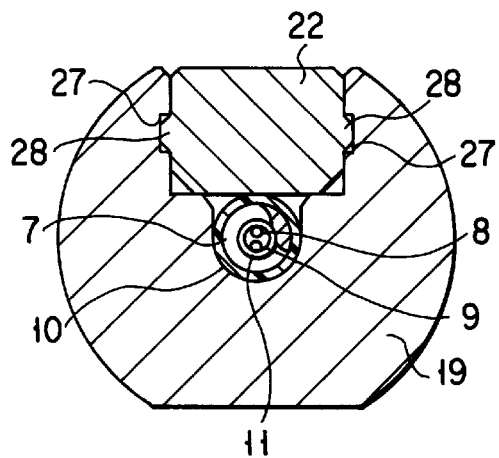
FIG. 18 is a sectional view taken along the line 18—18 of FIGS. 11 and 12.
Figure 19:
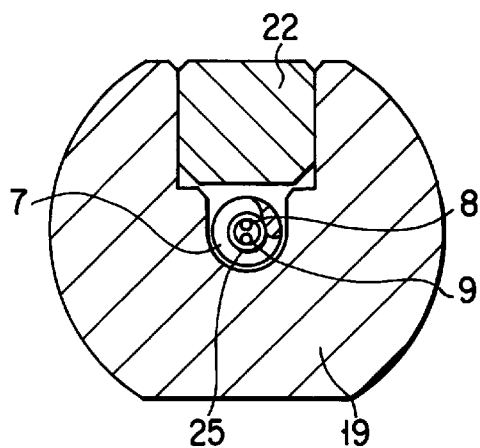
FIG. 19 is a sectional view taken along the line 19—19 of FIGS. 11 and 12.

As shown in FIGS. 13 to 15 and 17, the slider cover 21 is prevented from sliding off from the slider body 20 in the thrust direction by protrusions 34 formed on the slider 20. In order to realize assembly with no directional restriction, the slider body 20 and the slider cover 21 are respectively of a shape symmetrical with respect to a center axis of the operating section body 19. In order to prevent sinks on the slider body 20 and the slider cover 21 in the molding from occurring, through-holes 35 an 36 are respectively formed in the slider body 20 and the slider cover 21 to avoid an adverse influence of bulk shrinkage, as shown in FIGS. 15 to 17.

Figure 22:
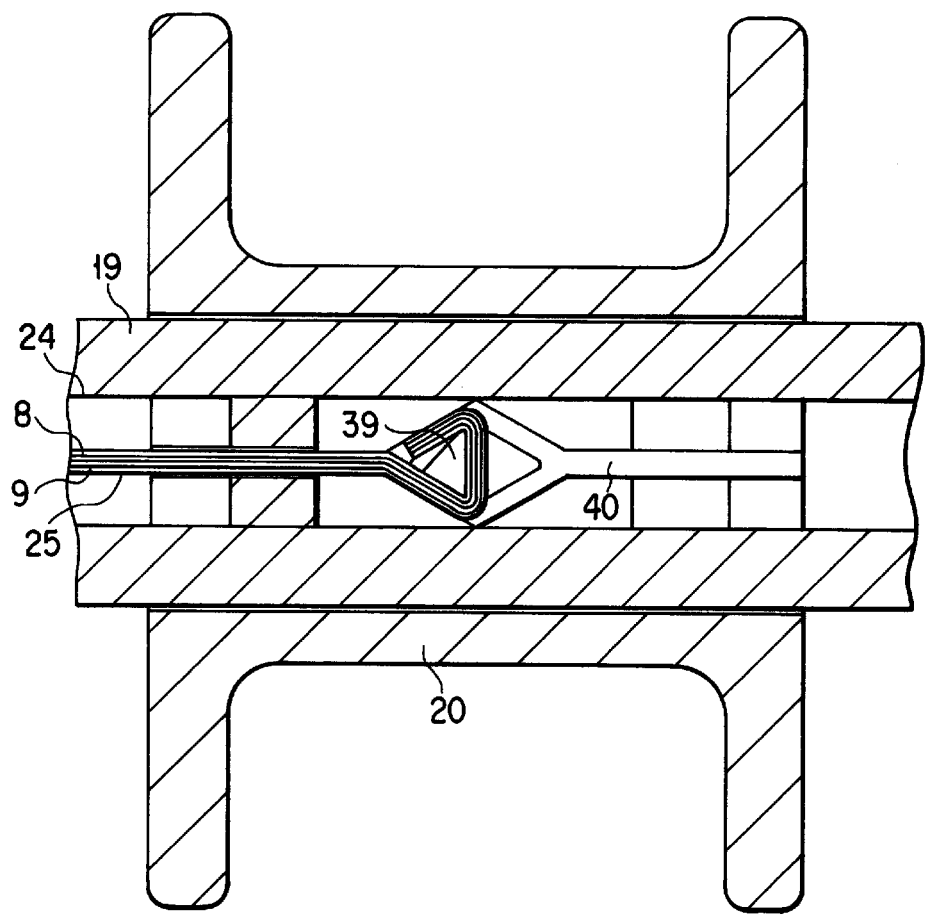
FIG. 22 is a sectional view showing a modification example of a locking structure of a pair of an operating pipe and a slider body.
Figure 23:
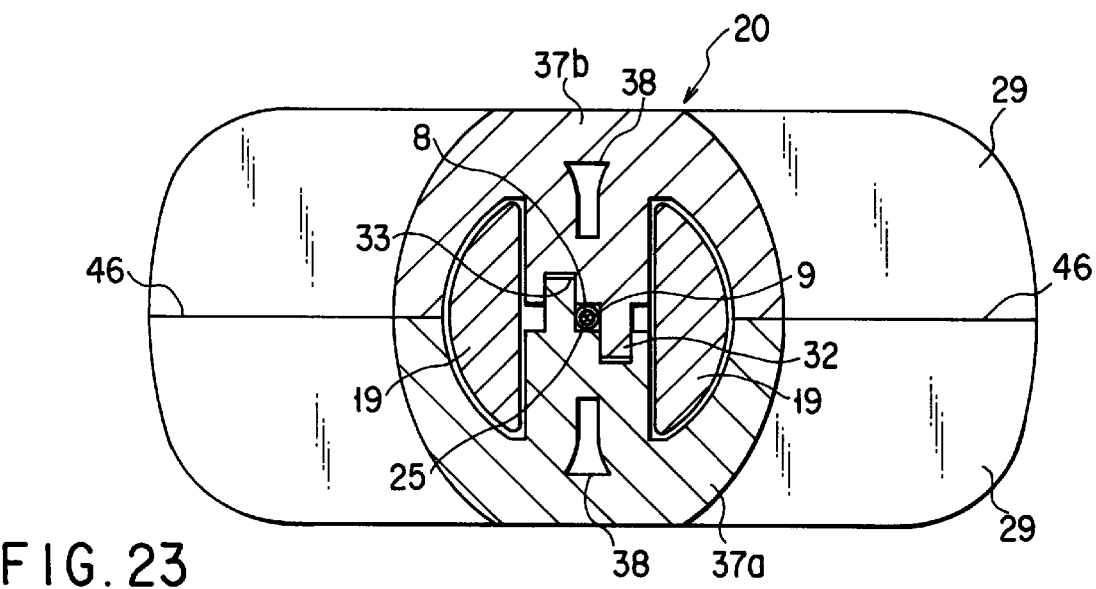
FIG. 23 is a sectional view showing a modification example of a joint structure of a pair of slider members.

As shown in FIG. 22, a structure may be adopted that the proximal end of the operating pipe 25 is bent like a hook together with the operating wires 8 and 9 and the hook-like portion is caught and locked by a protrusion 39 formed on the slider body 20. As shown in FIG. 23, another structure may also be adopted that the slider cover 21 is not provided but the slider body 20 is divided into two slider members 37a and 37b both having the same shape symmetric with respect to the center axis of the operating section body 19. A joint 46 between the two slider members 37a and 37b is fixed to each other by ultrasonic welding or the like. Further, through holes 38 are formed in the bulks of the slider members 37a and 37b to avoid an adverse influence of bulk shrinkage and thereby a sink in the molding of the slider members 37a and 37b. Grooves 33 formed on the slider members 37a and 37b and protrusions 32 formed on the slider members 37b (37a) are respectively engaged with each other and the stopper 30 is engaged with the recesses 44 and 45 formed in the almost center portions of the slider members 37a and 37b and thereby, the proximal ends of the operating wires 8 and 9 including the operating pipe 25 and the stopper 30 are fixed to the slider 43. With such a structure, assembly with no directional restriction can be realized and parts cost is suppressed low.

The operating section body 19, the slider body 20 (37), the slider cover 21 and the body cover 22 are all fabricated with a resin material that can be treated by thermal sterilization. Such resin materials can be named as follows, for example: polysulfone, polyphenylsulfone, polyetherimide, polytetrafluoroethylene (PTFE), tetrafluoroethyleneperfluoroalkoxy ethylene resin (PFA), tetrafluoroethylenehexafluoropropylene resin (FEP), polyacetal, poly(ether ether ketone) and others. Further, the operating section body 19, the slider body 20 (37), the slider cover 21 and the body cover 22 can be fabricated with the following materials: resin materials such as polyolefin, polycarbonate, acrylonitrile butadiene-styrene resin, polyamide, vinyl chloride, latex, polypropylene, polyethylene-terephthalate, ethylenevinyl acetate copolymer and natural rubber and in addition, mixtures thereof and cross-linked resins produced by irradiating the above exemplified resins with an electron beam. When the operating section body 19 and the slider body 20 (37), the slider cover 21 and the body cover 22 are made of such low cost materials of the latter group, they can be discarded after usage.

Then, description will be made of how the bioptome 1 with the above construction is operated.

When the slider 43 is slid on the operating body 19, the operating wires 8 and 9 connected to the slider 43 are moved forward or backward. When the operating wires 8 and 9 are moved forward or backward, the biopsy cups 4 and 5 connected to the distal ends of the operating wires 8 and 9 are rotated (opened or closed) about the pin 12 as a center, whereby a tissue sample can be taken from a body by the biopsy cups 4 and 5.

Figure 33:
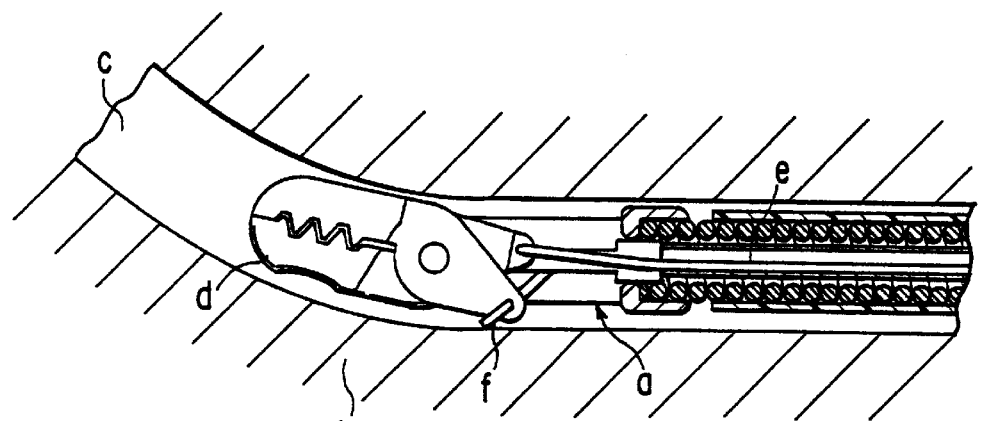
FIG. 33 is a sectional view showing a state in which a conventional endoscopic procedural device is inserted in the forceps-channel of an endoscope.

Further, if the endoscope is deformed and thereby, forceps-channel is bent like an arc as shown in FIG. 33 when the bioptome 1 remains inserted in the forceps-channel of the endoscope, the biopsy cups 4 and 5 are inclined to the cup holding member 6, connecting sections between the operating wires 8 and 9 and the biopsy cups 4 and 5 comes out of the slit section of the cup holding member 6, and the operating wires 8 and 9 are exposed. At this time, the operating wires 8 and 9 thus coming out of the slit section and being exposed are put into contact with the inner surface of the forceps-channel. According to this embodiment, however, the distal end portions of the operating wires 8 and 9 are first respectively inserted into the holes 15 through the first opening ends 48a of the holes 15 toward the center axis side of the insert sections 2 and then the distal ends are respectively protruded outside the holes 15 from the second opening ends 48b of the holes 15, and since the distal ends of the operating wires 8 and 9 are rounded, the inner surface of the forceps-channel is never damaged with the distal ends of the operating wires 8 and 9. Furthermore, the distal ends of the operating wires 8 and 9 protruded outside the holes 15 from the second opening ends 48b are located in the vicinity of the second opening ends 48b. That is, the operating wires 8 and 9 are inserted into the holes 15 from the first opening ends 48a and protruded out of the second opening ends 48b, and thereafter, are not extended toward the proximal end of the insert section 2. In other words, virtually one wire is connected to each of the biopsy cups 4 and 5. Hence, there arises no chance to make operability of the endoscopic procedural device heavy due to excessively high rigidity of the link wires 8 and 9.

As described above, according to this embodiment, the biopsy cups 4 and 5 can be opened and closed in a simple construction, mechanical processing and assembly are easy, and movements of the operating wires 8 and 9 are lightly effected. Furthermore, even when the bioptome 1 is inserted through the forceps-channel of an endoscope, the inner surface of the forceps-channel is not damaged by the distal ends of the operating wires and therefore, a procedure can be performed at ease.

In this embodiment, the distal end portions of the operating wires 8 and 9 are respectively inserted through the holes 15 from the first opening ends 48*a* toward the second opening ends 48*b*. However, when the distal ends of the operating wires 8 and 9 are formed in a shape not to damage the forceps-channel, a structure may be adopted in which the distal end portions of the operating wires 8 and 9 are respectively inserted through the holes 15 from the second opening ends 48*b* toward the first opening ends 48*a*.

FIGS. 26A to 28 show the second embodiment of the present invention.

This embodiment is a modification example of the first embodiment and what is different from the first embodiment is only a state of connection between the operating wires 8 and 9 and the biopsy cups 4 and 5. Hence, in this embodiment, constituent elements that are common with the first and second embodiments are indicated by the same reference marks and here, no descriptions are not given to the common constituent elements here.

Figure 28:
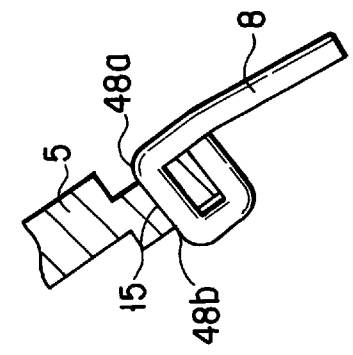
FIG. 28 is a view in a direction of arrow A of FIG. 26A.
Figure 31:
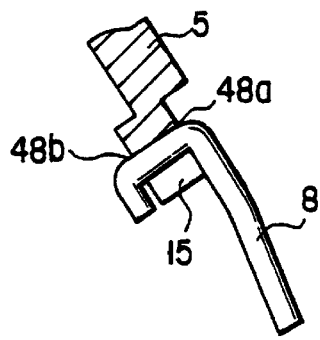
FIG. 31 is a view of a third modification example of the connecting state shown in FIG. 28.
Figure 32:
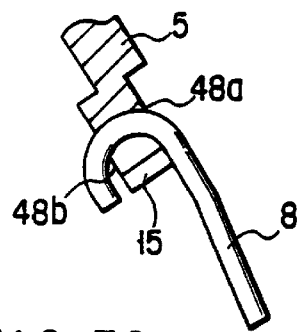
FIG. 32 is a view of a fourth modification example of the connecting state shown in FIG. 28.

As clearly shown in FIG. 28, the operating wires 8 and 9 are bent one time and then, the distal ends thereof are respectively inserted through the holes 15 from the first opening ends 48*a* at the proximal end sides of the biopsy cups 4 and 5 toward the center axis side of the insert section 2 and further protruded out of the second opening ends 48*b*. Further, the distal ends of the operating wires 8 and 9 are again bent toward the proximal end of the insert section 2 and still again, as a third time, bent toward extending directions of the holes 15, so that the distal end portions of the operating wires 8 and 9 are each shaped into a loop and thereby, the connections of the operating wires 8 and 9 with the biopsy cups 4 and 5 are completed with no future chance to be slipped off.

The other part of construction is same as that of the first embodiment. In FIGS. 29 to 32, another states of connection are shown between the operating wires 8 and 9 and the biopsy cups 4 and 5.

FIGS. 36 to 59 show the third embodiment of the present invention.

This embodiment is a modification example of the first embodiment and only a state of connection between the operating wires 8 and 9 and the biopsy cups 4 and 5 is different from the first embodiment. Hence, in this embodiment, common constituent elements with this embodiment and the first embodiment are indicated by the same reference marks and descriptions thereof are not given here.

Figure 36:
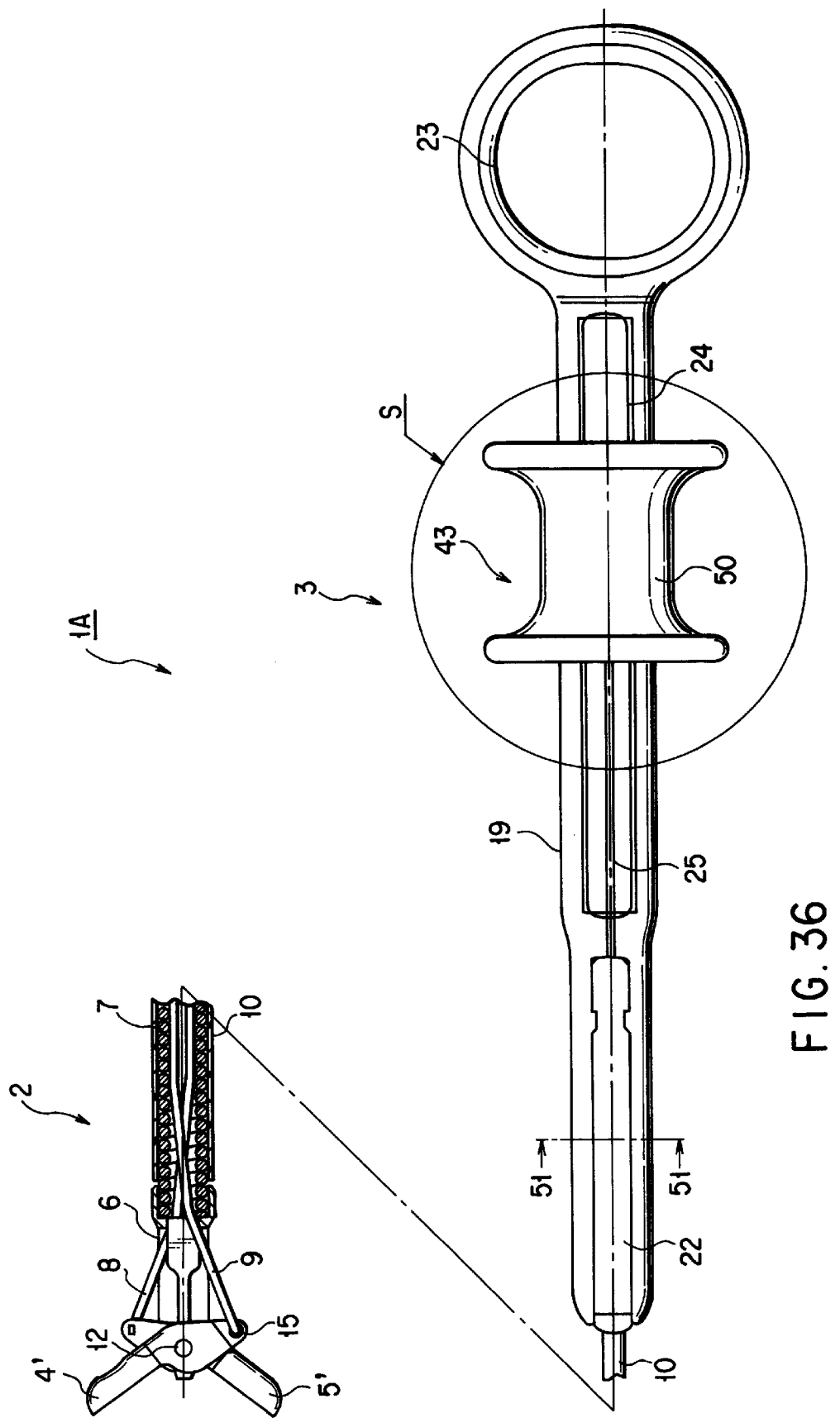
FIG. 36 is an overall view of construction of an endoscopic procedural device according to a third embodiment of the present invention.
Figure 40:
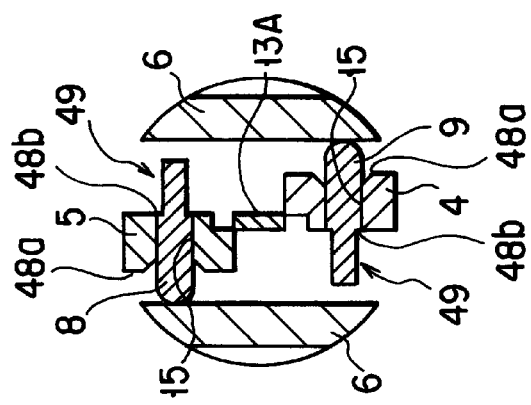
FIG. 40 is a sectional view taken on 40—40 of FIG. 37.
Figure 56:
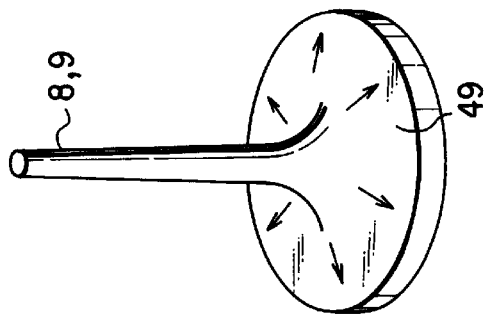
FIG. 56 is a perspective view of a modification example of a stopper section.

As shown in FIG. 36, a bioptome 1A of this embodiment comprises: an insert section 2 and an operating section 3. As shown in FIGS. 37 to 40, the distal end sections of operating wire 8 and 9 are respectively inserted into the holes 15 from first opening ends 48*a* of holes 15 formed at the proximal end sides of biopsy cups 4 and 5 toward the center axis side of the insert section 2, then the distal ends are protruded outside the holes 15 from second opening ends 48*b* of the holes 15 and the distal ends of the operating wire 8 and 9 are located in the vicinity of the second opening ends 48*b*. In order to prevent the operating wires 8 and 9 from being slipped off from the holes 15, stoppers 49 are formed at the tips of the distal ends of the operating wire 8 and 9 protruded outside the holes 15. The stoppers 49 are formed by deforming the distal end portions of the operating wire 8 and 9 by an external force such as a pressure and the outer diameters of the distal ends are set to be larger than an inner diameter of the holes 15 as shown in FIGS. 37, 38 and 40. For example, as shown in FIG. 56, a stopper 49 may be formed by enlarging each of the distal end portions of the operating wires 8 or 9 in all radial directions to form a flat shape under pressure on the distal ends of the operating wires 8 or 9 in a thrust direction.

In order to decrease an operating force for opening and closing of the biopsy cups 4 and 5, the operating wires 8 and 9 respectively have bending sections 100A and 100B, one for each, mechanically processed each with three bending angles $\theta_1$ to $\theta_3$ as shown in FIGS. 37 and 38, wherein the three angles are desirably set in the following angular ranges:

$\theta_1 \geq 50°$ $140° < \theta_2 < 180°$ $0° < \theta_3 < 50°$

Figure 54:
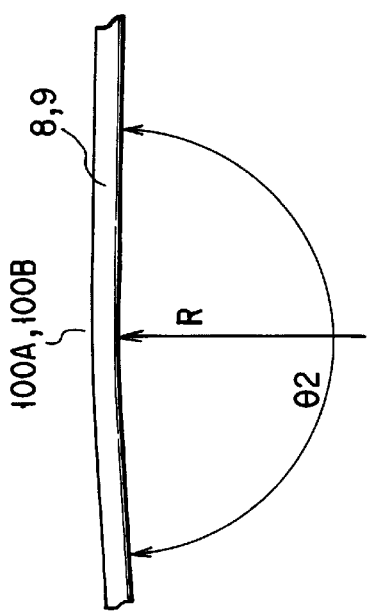
FIG. 54 is an illustration of a first modification in a bending angle of operating wires.

Furthermore, the bending sections 100A and 100B, as shown in FIG. 54, are bent with a radius R of curvature of 0.05 mm or more at bending points so that bending is effected in a rounded shape around the bending points in order to decrease an operating force to open or close the biopsy cups 4 and 5 and in order to prevent the bending sections of the operating wires 8 and 9 from interfering with each other in the opening or closing of the biopsy cups 4 and 5.

Figure 57:
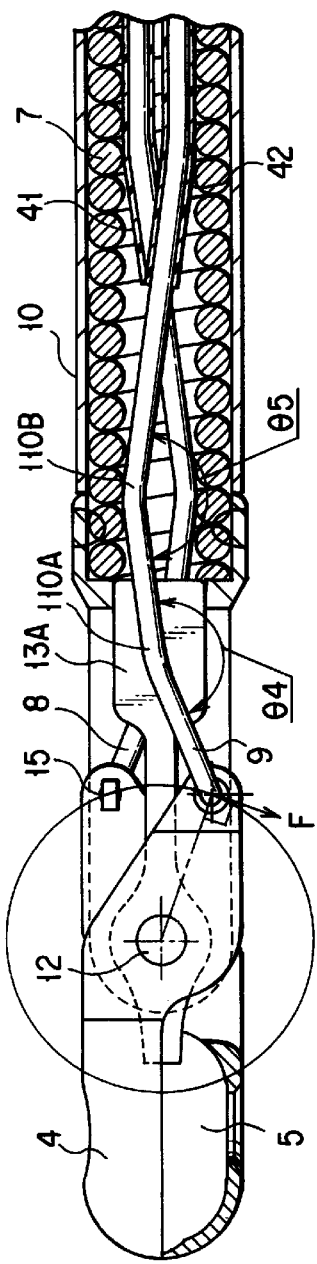
FIG. 57 is a view showing a second modification example of a bending angle of operating wires.

As shown FIG. 57, the operating wires 8 and 9 may respectively have two bending sections 110A and 110B that are respectively with two angles $\theta_4$ and $\theta_5$. If the two bending sections 110A and 110B are provided to each of the operating wires 8 and 9, the mechanism can have a large torque F in a tangential direction of a circle with a pin 12 as a center, which torque is required when the biopsy cups 4 and 5 are rotated, and can prevent the bending sections of the operating wires 8 and 9 from interfiring with the engaging section between the cup holding member 6 and a needle 13 (which means to deteriorate operatbility of the operating wires 8 and 9). In this case, $\theta_4$ and $\theta_5$ are set in the following angular ranges:

$140° < \theta_4 < 180°$ $140° < \theta_5 < 180°$

Figure 58:
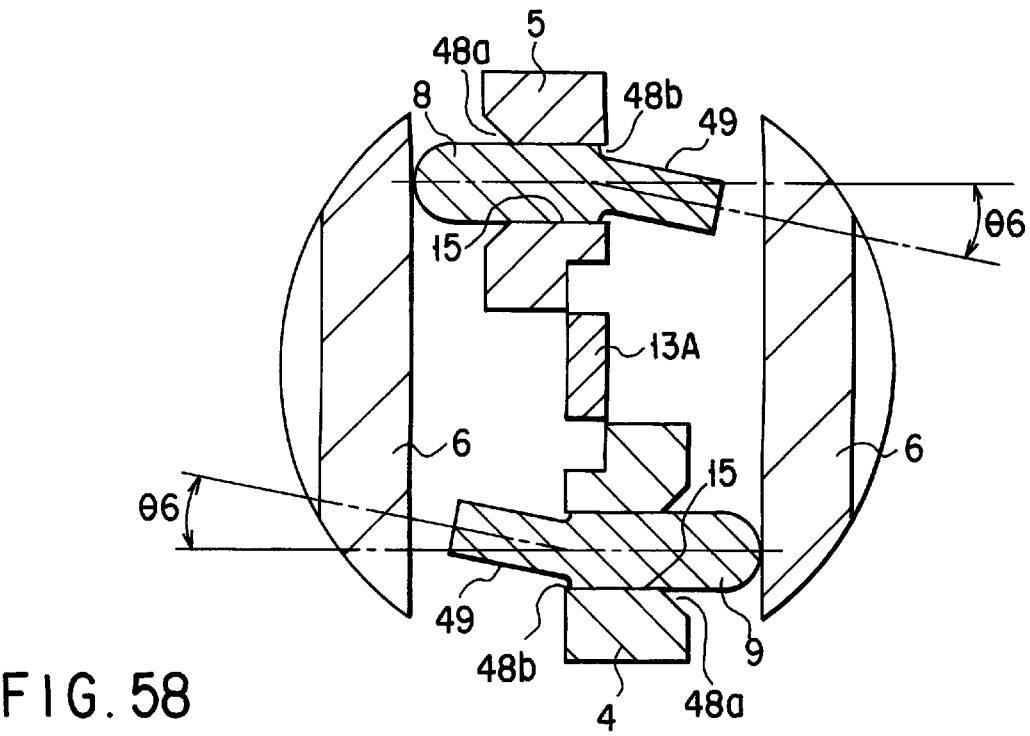
FIG. 58 is a sectional view of a first modification example of a connecting structure of biopsy cups and operating wires of an endoscopic procedural device of a third embodiment.
Figure 59:
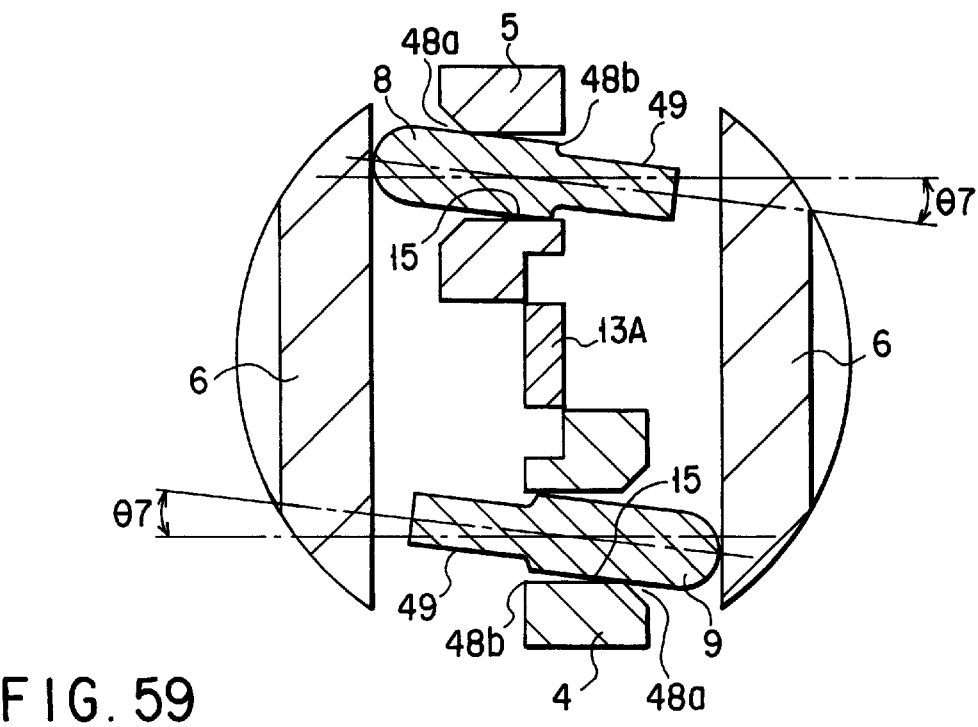
FIG. 59 is a sectional view of a second modification example of the connection structure of a biopsy cups and operating wires of an endoscopic procedural device of a third embodiment.

Further, the stopper 49, as shown in FIG. 58, may be inclined at a prescribed angle $\theta_6$ so that the stopper 49 does not damage the forceps-channel of the endoscope, or alternatively, the distal end portions of the operating wires 8 and 9 inserted through the holes 15 may be inclined at a prescribed angle $\theta_7$ together with the stopper 49. In this case, $\theta_6$ and $\theta_7$ are desirably set in the following ranges:

$0° < \theta_6 < 90°$ $0° < \theta_7 < 90°$.

Figure 41:
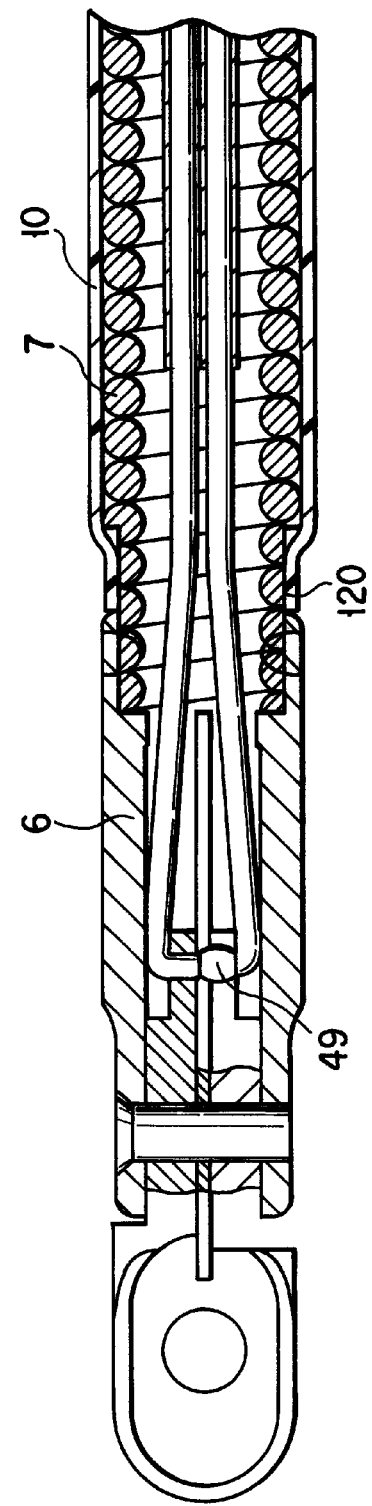
FIG. 41 is a sectional view of a modification example of a joint structure of a cup holding member and a coil.

The cup holding member 6 and the coil 7, as shown in FIG. 41, are connected to each other while engaging in order to improve a flexibility of the coil 7 and increase easiness of insertion of the insert section 2 into the forceps-channel of the endoscope. That is, a small diameter section 120 longer than an engaged length between the cup holding member 6 and the coil 7 may be formed at the distal end portion of the coil 7 by scraping off an outer surface portion of the distal end side of the coil 7 (by reducing an element wire diameter of the coil 7).

Figure 42:
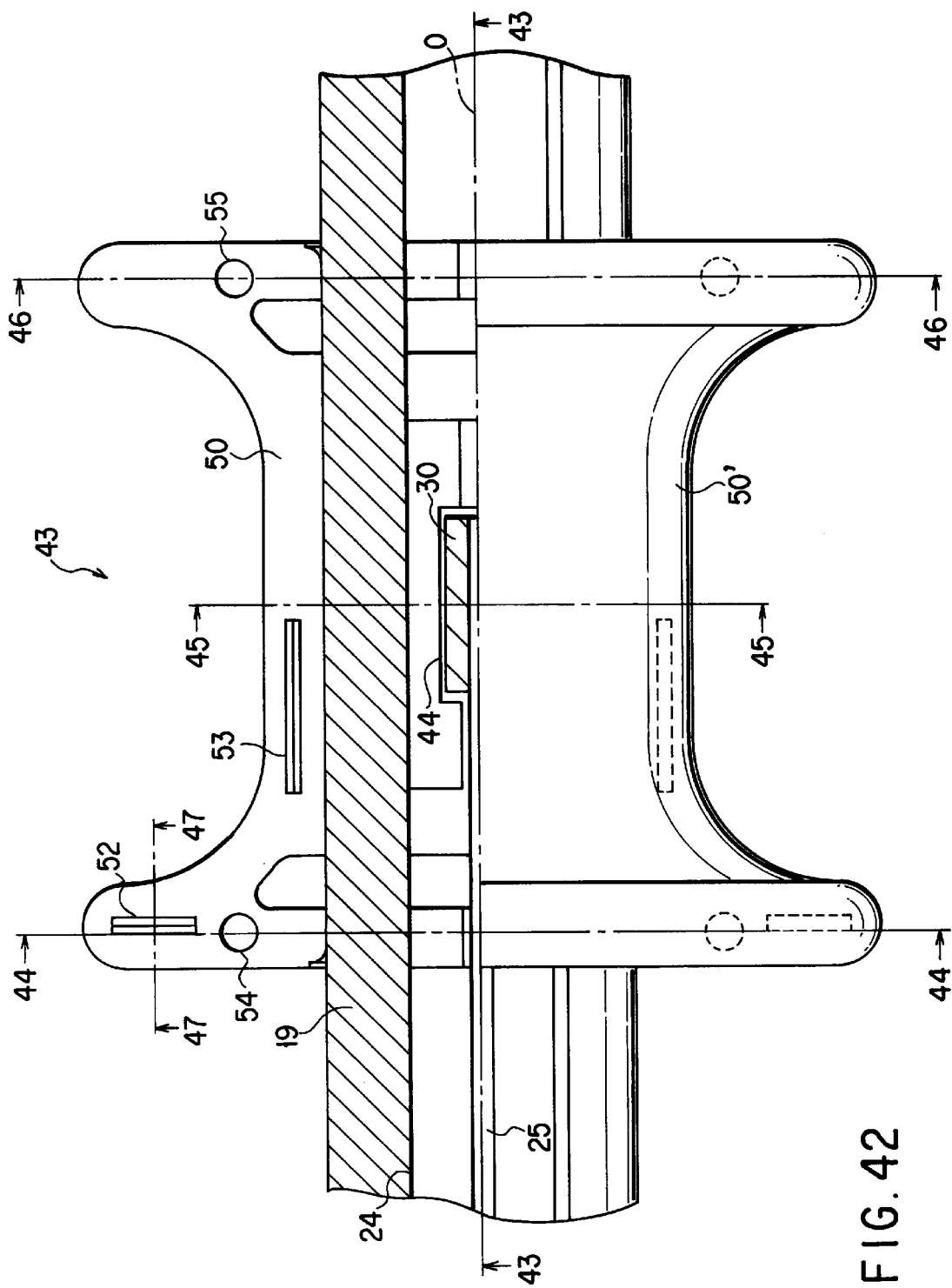
FIG. 42 is a detailed view of part S of FIG. 36 (the upper half only is shown in section)
Figure 43:
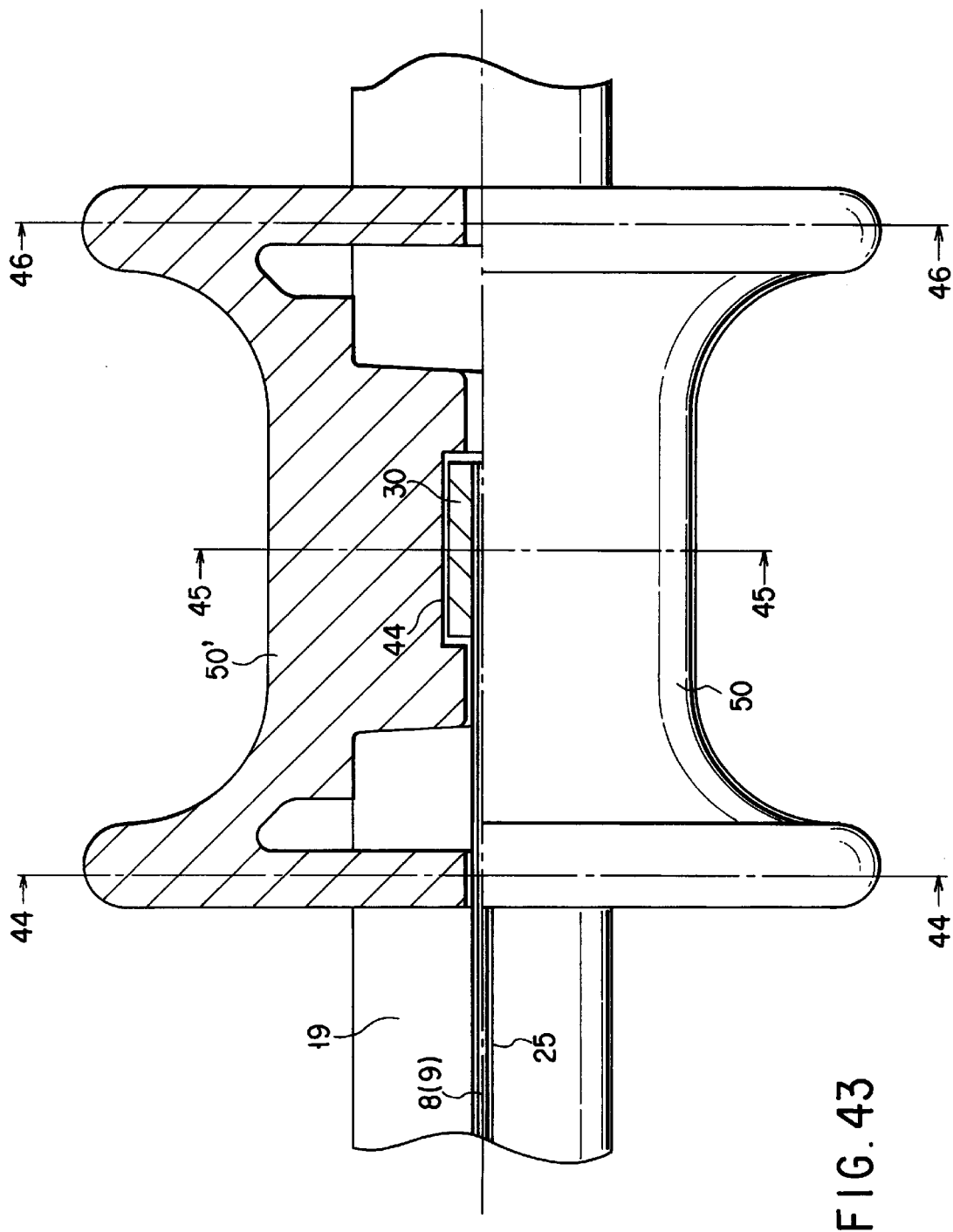
FIG. 43 is a sectional view taken along the line 43—43 of FIG. 42.
Figure 44:
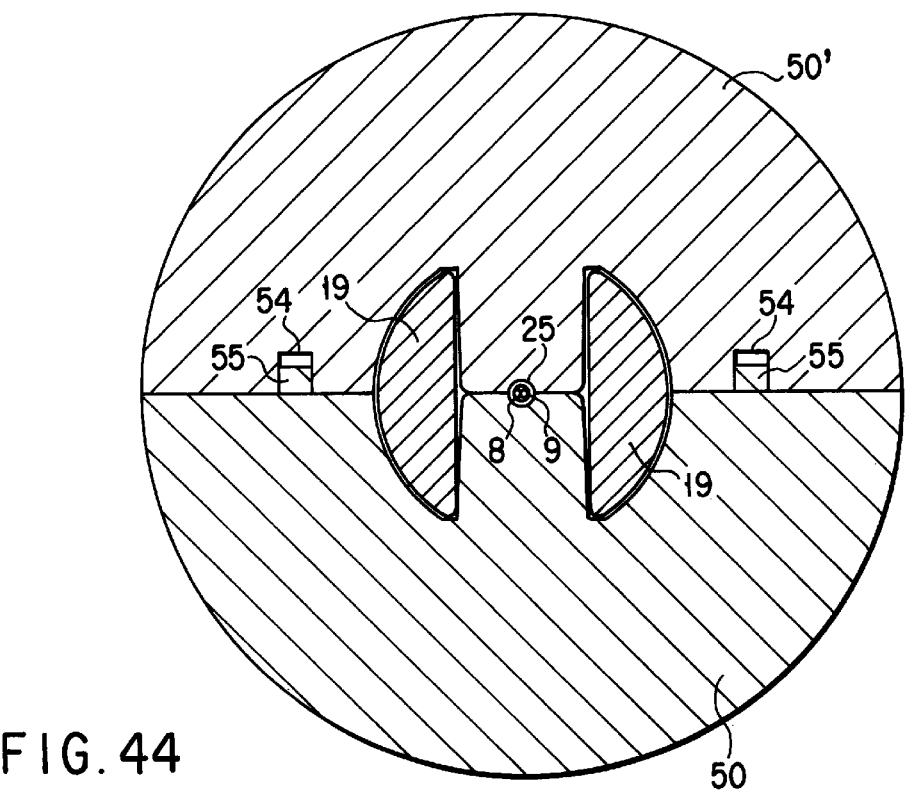
FIG. 44 is a sectional view taken along the line 44—44 of FIGS. 42 and 43.
Figure 45:
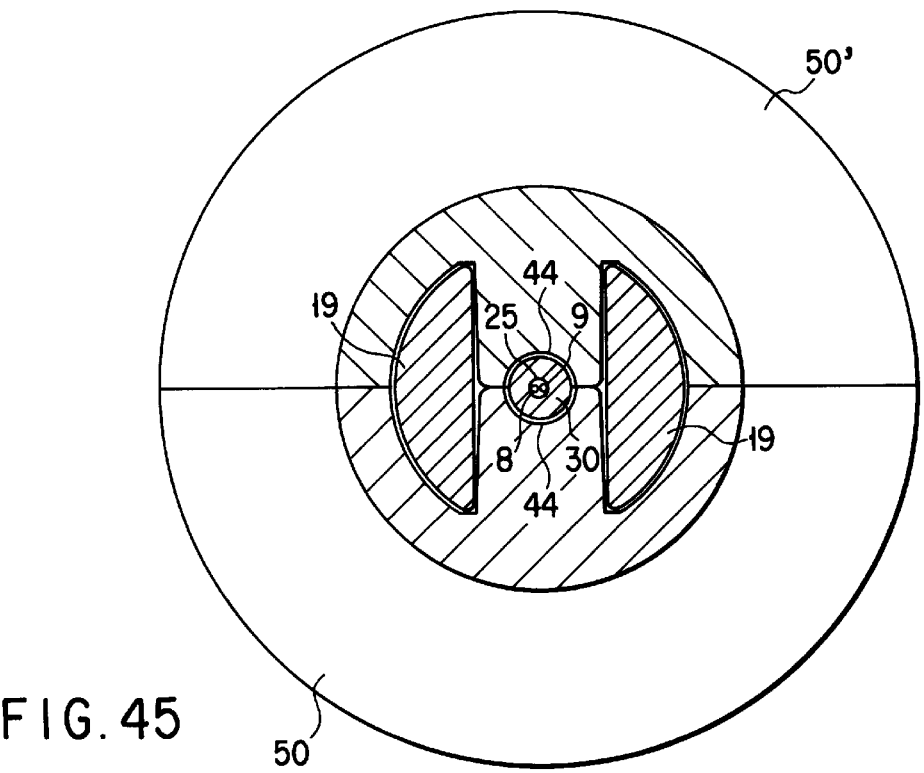
FIG. 45 is a sectional view taken along the line 45—45 of FIGS. 42 and 43.
Figure 46:
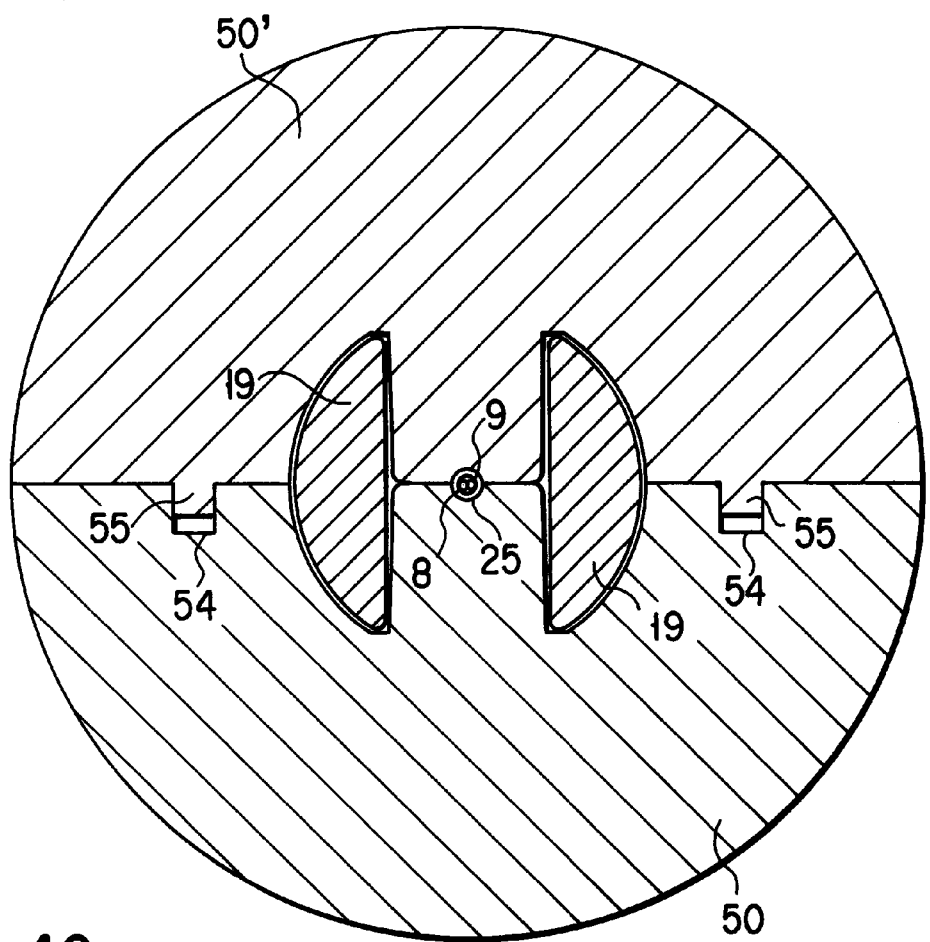
FIG. 46 is a sectional view taken along the line 46—46 of FIGS. 42 and 43.

The operating section 3 comprises: an operating section body 19 and a slider 43 as shown in FIGS. 42, 43 and 45. The proximal end sides of the operating wires 8 and 9 are inserted through the inside hole of the operating pipe 25. Further, the proximal end section of the operating pipe 25 is inserted into the operating pipe 30 having a cylindrical shape. The operating wires 8 and 9, the operating pipe 25 and the stopper 30 are integrated by means of plasma welding, laser welding or the like into one body.

A slider 43 comprises: two slider members 50 and 50' and can slide on rails each having a half-moon shape of the operating section body 19 having grooves 24. As shown in FIGS. 42 to 46, a recess 54 (or a protrusion 55) formed on the slider member 50 and a protrusion 55 (or a recess 54) formed on the slider member 50' are respectively engaged with each other, and not only the stopper 30 is engaged with recesses 44 and 44 respectively formed in the almost middle sections of the slider members 50 and 50', but welding protrusions 52 and 53 respectively provided on the slider members 50 and 50' are molten by an ultrasonic welder or the like to join the slider members 50 and 50', whereby the distal ends of the operating wires 8 and 9 including the operating pipe 25 and the stopper 30 are fixed to the slider 43.

Figure 47:
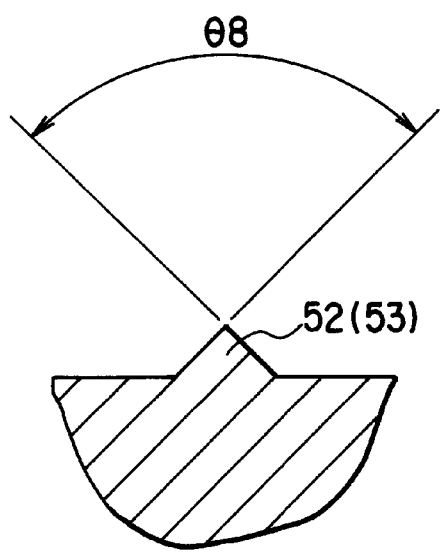
FIG. 47 is a sectional view taken along the line 47—47 of FIG. 42.

As shown in FIG. 47, the welding protrusions 52 and 53 respectively have a sectional shape of a triangle so as to be easily welded. Angles $\theta_8$ included between two sides at the apex of the protrusions 52 and 54 are desirably set in the following angular range:

$$0° < \theta_8 < 180°.$$

As shown in FIG. 42, the welding protrusions 52 and 53 are respectively located on the slider members 50 and 50' symmetrically with respect to the center axis O of the slider 43. The protrusions 55 and the recesses 54 are respectively located symmetrically with respect to the center axis O of the slider 43 as well. Therefore, the slider members 50 and 50' can be fabricated in the same shape, which enables the number of parts to be reduced.

Figure 48:
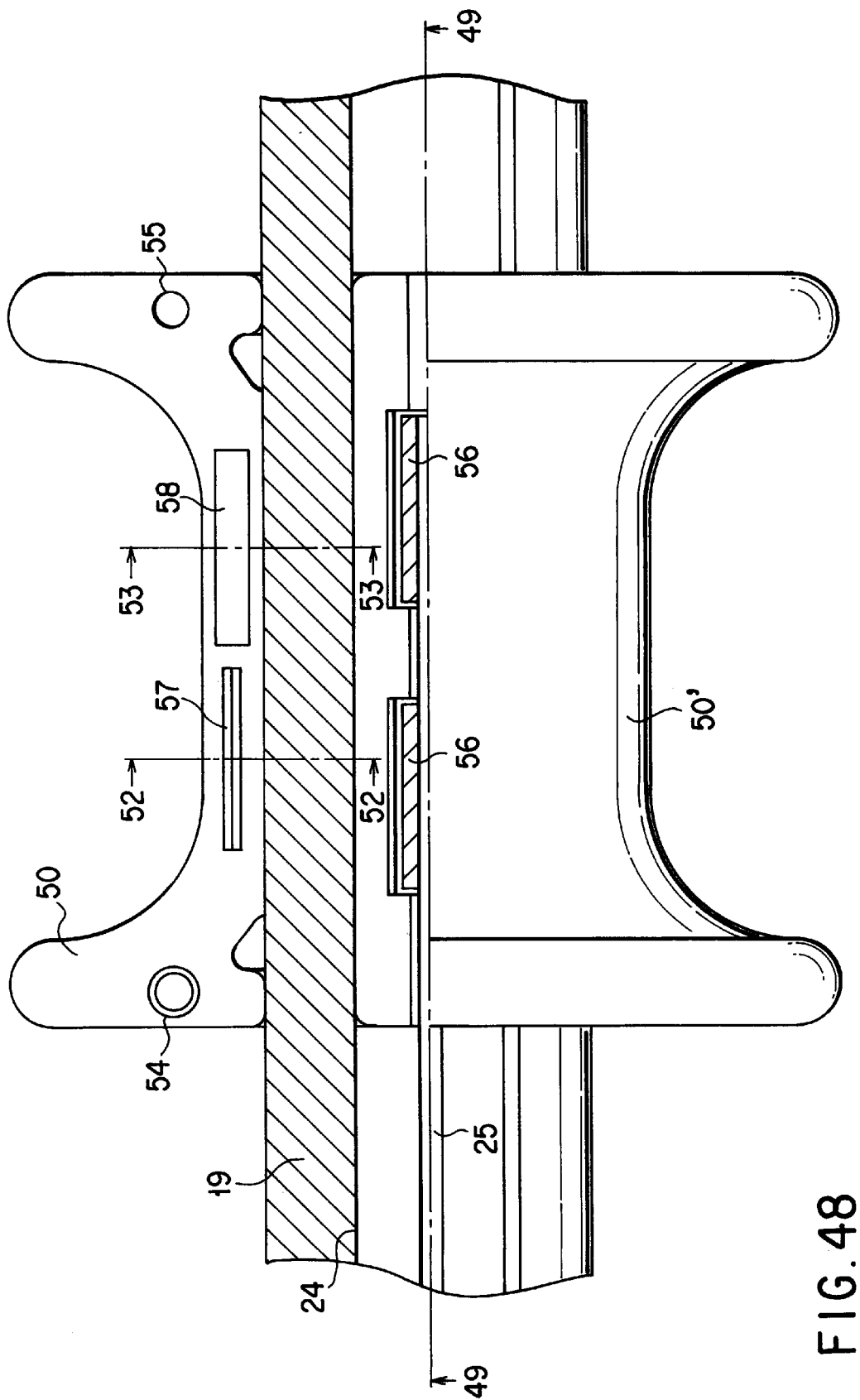
FIG. 48 is a sectional view of a modification example in structure of FIG. 42.
Figure 49:
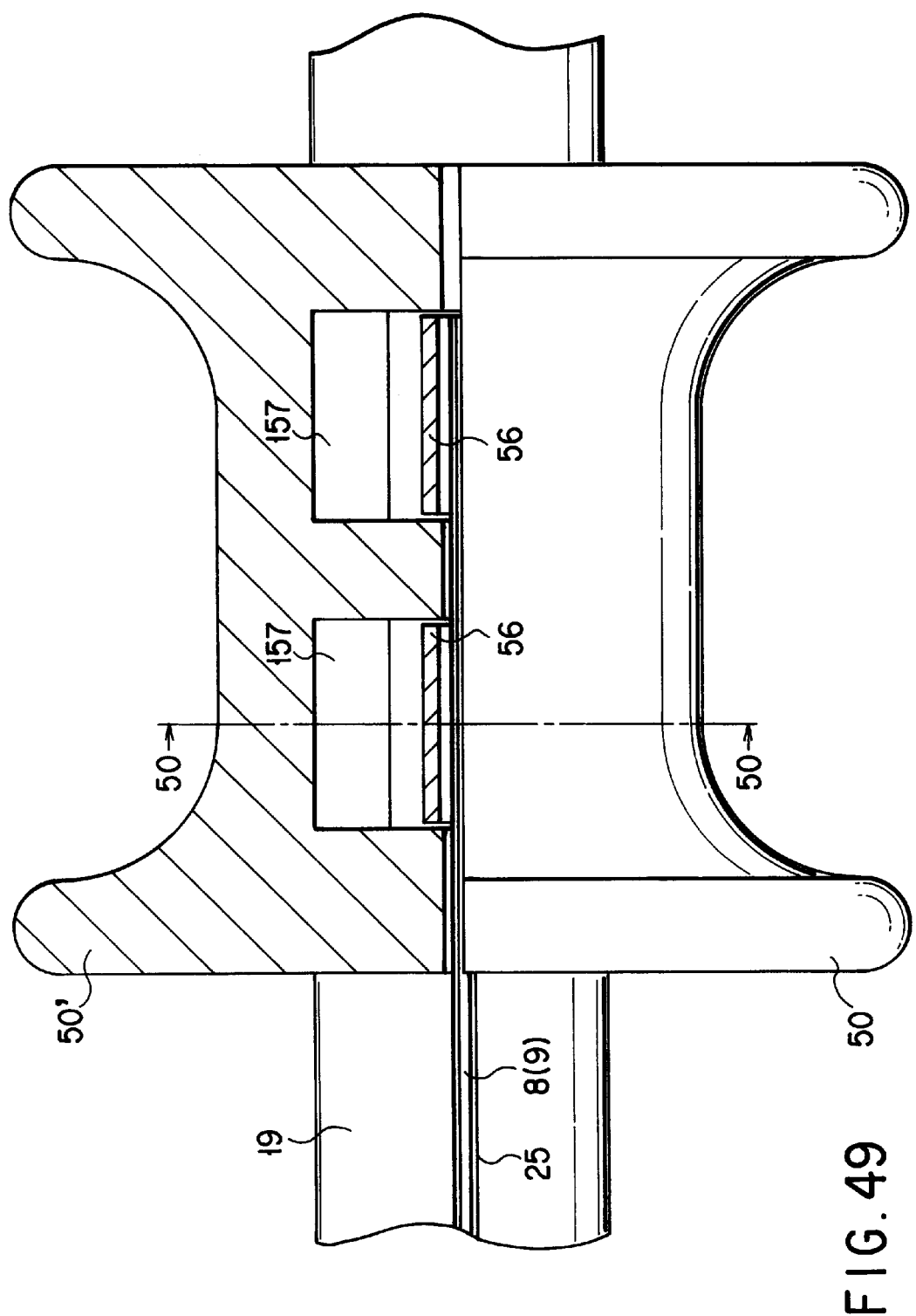
FIG. 49 is a sectional view taken along the line 49—49 of FIG. 48.
Figure 50:
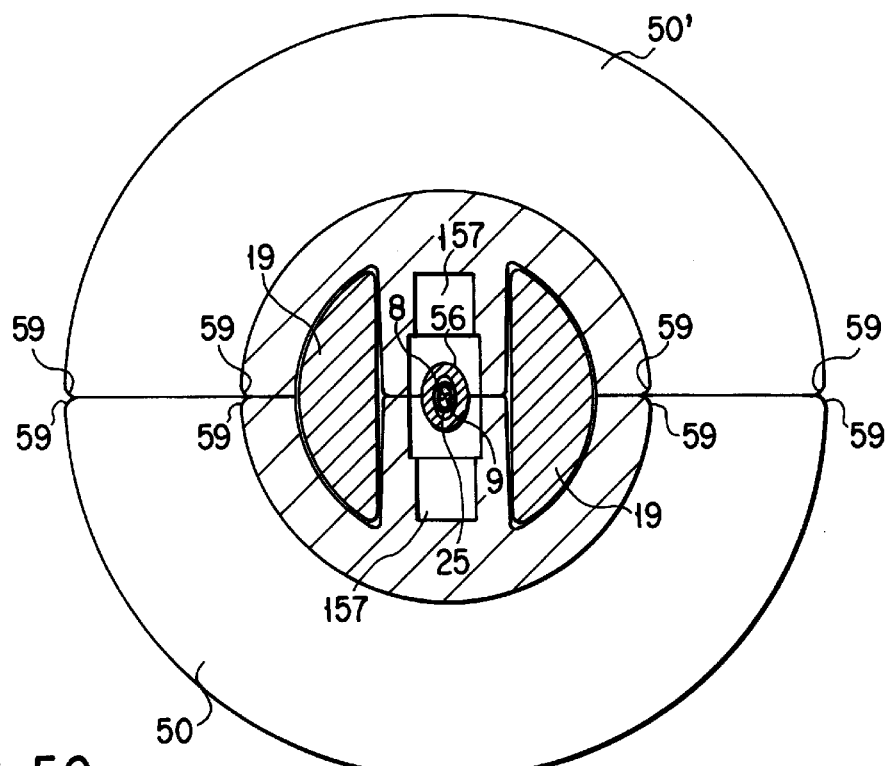
FIG. 50 is a sectional view taken along the line 50—50 of FIG. 49.
Figure 51:
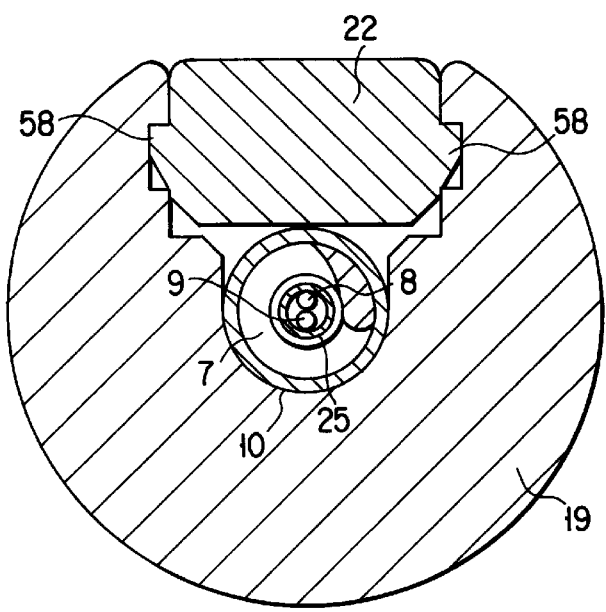
FIG. 51 is a sectional view taken along the line 51—51 of FIG. 36.
Figure 52:
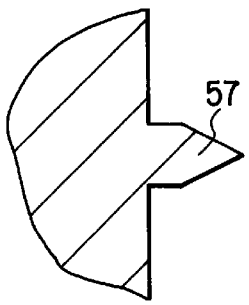
FIG. 52 is a sectional view taken along the line 52—52 of FIG. 48.

A modification example of the operating section 3 is shown in FIGS. 48 to 50. As shown in the figure, in this modification example, in order to increase a strength of the operating section 3, stoppers 56 are fixed through caulking at two positions on the operating pipe 25 using one of an autosplicer and any of kinds of other caulking devices. Conditions to improve a caulking strength are such that a thickness and width of the stopper 56 are preferably in the range of 0.1 mm to 1.0 mm and in the range of 1 mm to 10 mm respectively.

Figure 53:
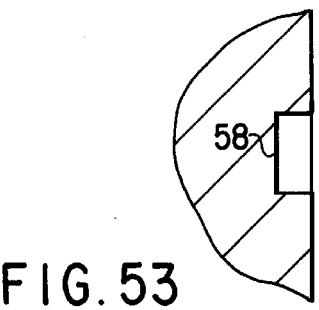
FIG. 53 is a sectional view taken along the line 53—53 of FIG. 48.

Even when the base of a protrusion 55 is rounded so that the protrusion 55 can be easy to be inserted, the opening end of the corresponding recess 54, which end serves positioning of the members 50 and 50' in assembly thereof, is preferably chamfered or provided with a clearance groove so that no clearance occurs between the slider members 50 and 50' because of geometrical interference with each other. Further, clearance grooves 58, as shown in FIGS. 48 and 53, for accepting a molten mass are provided on the slider members 50 and 50' so that no gaps arise at the interface between the slider members 50 and 50' when welding protrusions 57 are molten. Groove clearances 157 as shown in FIGS. 49 and 50 are formed in the slider members 50 and 50' so that the slider members 50 and 50' are not affected by sinks. In order to alleviate dimensional discrepancy in appearance between the slider members 50 and 50' in assembly, the peripheral edge portions 59 of the slider members are rounded (see FIG. 50). Instead of roundings 59, the peripheral edge portions of the slider members 50 and 50' may be formed so as to have recesses such as clearance grooves or cosmetic grooves).

Figure 55:
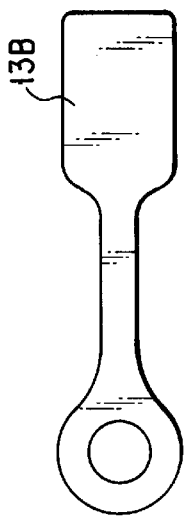
FIG. 55 is a side view showing an modification example of a needle.

A needle 13A has a shape as shown in FIG. 37. That is, the needle 13A is prepared by cutting a fore-end of a needle 13 shown in FIG. 3 with a nipper or the like. Further, a needle 13B as shown in FIG. 55 may be employed and the needle 13B is fabricated, for example, using a press die.

The present invention can be applied not only to the bioptome shown in the above described embodiments, but to grasp forceps, cutting forceps, hot biopsy forceps and others.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic procedural device comprising:
   an insert section that has an inside hole extending along its axial direction, and which has flexibility to enable its insertion through a forceps-channel of an endoscope;
   at least one operating wire that is inserted in the inside hole of the insert section, and which is freely moved forward or backward along the axial direction of the insert section;
   an operating section that is connected to a proximal end of the insert section, and which is used for moving the operating wire forward or backward;
   a procedural section holding member connected to a distal end of the insert section;
   at least one procedural member that is mounted to a distal end of the procedural section holding member in a rotatable manner, and which has one through-hole at its proximal end side to which one of the operating wires is connected,
   wherein the one through-hole has a first opening end, on one side of a procedural member, at a position farther from the center axis of the insert section, and a second opening end, on the other side of the procedural member, at a position closer to the center axis of the insert section, and
   a distal end portion of an operating wire is not only inserted into the one through-hole toward the center axis side of the insert section from the first opening end, but protruded outside the one through-hole from the second opening end and the protruded distal end portion of the operating wire is positioned in the vicinity of the second opening end.

2. An endoscopic procedural device according to claim 1, wherein the distal end of an operating wire protruded from the second opening end of the one through-hole is rounded.

3. An endoscopic procedural device according to claim 1, wherein the distal end of an operating wire is bent at least one time and then inserted into the one through-hole from the first opening end.

4. An endoscopic procedural device according to claim 1, further comprising:
   wire slip-off preventing means for preventing the operating wire from being slip off from the one through-hole.

5. An endoscopic procedural device according to claim 4, wherein the wire slip-off preventing means is constituted of a stopper that is formed at the distal end of the operating wire protruded from the second opening end of the one through-hole and whose outer diameter is larger than an inner diameter of the one through-hole.

6. An endoscopic procedural device according to claim 5, wherein the stopper is fixed at the distal end of an operating wire by welding or gluing.

7. An endoscopic procedural device according to claim 5, wherein the stopper is formed in a spherical shape.

8. An endoscopic procedural device according to claim 5, wherein the stopper is formed in a flat shape by deforming the distal end portion of the operating wire by a pressure.

9. An endoscopic procedural device according to claim 5, wherein the stopper is formed by enlarging the distal end portion of an operating wire in all radial directions to form a flat shape under pressure on the distal end portion of the operating wire in a thrust direction.

10. An endoscopic procedural device according to claim 1, wherein the distal end of an operating wire protuding from the second opening end of the one through-hole is bent toward a proximal end side of the insertion section so as to be shaped into a loop.

11. An endoscopic procedural device according to claim 1, wherein a pair of procedural members that work in a cooperative manner with each other are rotatably mounted to the distal end portion of the procedural section holding member and operating wires inserted through the insert section are respectively connected to the through-holes of the procedural members.

12. An endoscopic procedural device according to claim 11, wherein a first operating wire and a second operating wire that are at the same time moved forward or backward by the operating section are inserted in the insert section and the first operating wire is connected to the one through-hole of one procedural member and the second operating wire is connected to the one through-hole of the other procedural member.

13. An endoscopic procedural device according to claim 12, further comprising:

a flexible tube that is inserted through the insert section so as to be freely moved forward or backward, and which has an inside hole through which the first and second operating wires are inserted.

14. An endoscopic procedural device according to claim 13, wherein the flexible tube is made of one, or a mixture of two or more selected from the group consisting of polytetrafluoroethylene (PTFE), tetrafluoroethylene-perfluoroalkoxy ethylene resin (PFA), tetrafluoroethylene-hexafluoropropylene resin (FEP), polyethylene, polypropylene, polyethylene-terephthalate, ethylene-vinyl acetate copolymer, polyolefin, polyamide, vinyl chloride, latex and natural rubber.

15. An endoscopic procedural device according to claim 1, wherein the insert section comprises: a coil made of one, or alloy of two or more selected from the group consisting of stainless, aluminum, nickel, brass, titanium, iron, phosphor bronze, tungsten, gold, silver and copper.

16. An endoscopic procedural device according to claim 15, wherein an outer surface of the coil is covered with a tube made of one, or a mixture of two or more selected from the group consisting of polytetrafluoroethylene (PTFE), tetrafluoroethylene-perfluoroalkoxy ethylene resin (PFA), tetrafluoroethylene-hexafluoropropylene resin (FEP), polyethylene, polypropylene, polyethylene-terephthalate, ethylene-vinyl acetate copolymer, polyolefin, polyamide, vinyl chloride, latex and natural rubber.

17. An endoscopic procedural device comprising:

an insert section that has an inside hole extending along its axial direction through a forceps-channel of an endoscope;

at least one operating wire that is inserted in the inside hole of the insert section, and which is freely moved forward or backward along the axial direction of the insert section;

an operating section that is connected to a proximal end of the insert section, and which is used for moving the operating wire forward or backward;

a procedural section holding member connected to a distal end of the insert section;

at least one procedural member that is mounted to a distal end of the procedural section holding member in a rotatable manner, and which has one through-hole at its proximal end side to which one of the operating wires is connected, wire slip-off preventing means for preventing the operating wire from being slipped off from the one through-hole, wherein the distal end of an operating wire is bent at least one time and then inserted into the one through-hole toward the center axis side of the insert section.

18. An endoscopic procedural device according to claim 17, wherein the wire slip-off preventing means is constituted of a stopper that is formed at the distal end of the operating wire and whose outer diameter is larger than an inner diameter of the one through-hole.

19. An endoscopic procedural device according to claim 18, wherein the stopper is formed in a flat shape by deforming the distal end portion of the operating wire by a pressure.

20. An endoscopic procedural device comprising:

an insert section that has an inside hole extending along its axial direction, and which has flexibility to enable its insertion through a forceps-channel of an endoscope;

at least one operating wire that is inserted in the inside hole of the insert section, and which is freely moved forward or backward along the axial direction of the insert section;

an operating section that is connected to a proximal end of the insert section, and which is used for moving the operating wire forward or backward;

a procedural section holding member connected to a distal end of the insert section;

at least one procedural member that is mounted to a distal end of the procedural section holding member in a rotatable manner, and which has one through-hole at its proximal end side to which one of the operating wires is connected, wherein the distal end of an operating wire that is inserted in the one through-hole is bent toward a proximal end side of the insertion section so as to be shaped into a loop.

* * * * *